US012770634B2

(12) United States Patent
Yasin et al.

(10) Patent No.: US 12,770,634 B2
(45) Date of Patent: Oct. 20, 2026

(54) NEURAL-INSPIRED AUDIO SIGNAL PROCESSOR

(71) Applicant: UCL VENTURES LIMITED, London (GB)

(72) Inventors: Ifat Yasin, London (GB); Vit Drga, London (GB)

(73) Assignee: UCL VENTURES LIMITED, London (GB)

( * ) Notice: Subject to any disclaimer, the term of this patent is extended or adjusted under 35 U.S.C. 154(b) by 82 days.

(21) Appl. No.: 18/705,774

(22) PCT Filed: Oct. 28, 2022

(86) PCT No.: PCT/EP2022/080302
§ 371 (c)(1),
(2) Date: Apr. 29, 2024

(87) PCT Pub. No.: WO2023/078809
PCT Pub. Date: May 11, 2023

(65) Prior Publication Data

US 2025/0046325 A1 Feb. 6, 2025

(30) Foreign Application Priority Data

Nov. 5, 2021 (GB) ..................................... 2115950

(51) Int. Cl.
*G10L 21/0208* (2013.01)
*A61B 5/372* (2021.01)

(52) U.S. Cl.
CPC .......... *G10L 21/0208* (2013.01); *A61B 5/372* (2021.01); *G10L 2021/02087* (2013.01)

(58) Field of Classification Search
CPC ....... G10L 21/0208; G10L 2021/02087; G10L 21/00; G10L 21/003; G10L 21/0224;
(Continued)

(56) References Cited

U.S. PATENT DOCUMENTS 6,732,073 B1 * 5/2004 Kluender ............. H04R 25/505 704/233
11,322,167 B2 * 5/2022 Healy ................. G10L 21/0232
(Continued)

FOREIGN PATENT DOCUMENTS

WO 2015169649 A1 11/2015

OTHER PUBLICATIONS

Mclachlan et al., ("Enhancement of speech perception in noise by periodicity: A neurobiological model and signal processing algorithm", Speech Communication, vol. 57, 2013, pp. 114-125). (Year: 2013).*

(Continued)

*Primary Examiner* — Vijay B Chawan
(74) *Attorney, Agent, or Firm* — POLSINELLI LLP

(57) ABSTRACT

An audio-signal processor (100) for filtering an audio signal-of-interest from an input audio signal (111) comprising a mixture of the signal-of-interest and background noise, the processor (100) comprising a frontend unit (120), the frontend unit (120) comprising a filterbank (121) comprised of an array of bandpass filters, a sound level estimator (123), and a memory (122) with one or more input-output, I/O, functions stored on said memory (122); wherein the frontend unit (120) is configured to receive:

an unfiltered input audio signal (111), and
human-derived neural-inspired feedback signals, NIFS, wherein the frontend unit (120) is further configured to:

extract sound level estimates from an output of the one or more bandpass filters using the sound level estimator (123),
modify the input-output, I/O, functions in response to the received sound level estimates and the NIFS, and determine an enhanced I/O functions, and
store the enhanced I/O functions on the memory (122) and use the enhanced I/O functions to determine one or (Continued)

more modified filterbank parameters in response to the received NIFS and sound level estimates, apply the modified filterbank parameters either across one filter in the filterbank (121) or across a range of filters in the filterbank (121) within the frontend unit (120), and output a filtered audio signal (112) to a sound feature onset detector (130) for further processing.

22 Claims, 7 Drawing Sheets

(58) Field of Classification Search
CPC ..... G10L 21/0232; G10L 25/30; G10L 25/15; G10L 21/0364; G10L 25/48; G10L 25/84; G10L 25/60; A61B 5/372; A61B 2505/09; H04R 2225/43; H04R 25/505; H04R 1/1083
USPC .......................................................... 704/226
See application file for complete search history.

(56) References Cited

U.S. PATENT DOCUMENTS

| | | | | |
|---|---|---|---|---|
| 12,009,005 B2 * | 6/2024 | Thiemt | G10L 25/84 |
| 2007/0226621 A1 * | 9/2007 | Dayan | G06Q 30/02 715/706 |
| 2019/0251971 A1 * | 8/2019 | Visser | G10L 13/047 |
| 2025/0046325 A1 * | 2/2025 | Yasin | A61B 5/372 |
| 2025/0070724 A1 * | 2/2025 | Ishihara | H03F 1/565 |

OTHER PUBLICATIONS

International Search Report and Written Opinion mailed Feb. 15, 2023 in International Application PCT/EP2022/080302.
Mclachlan Neil M. et al., "Enhancement of 1,3-5, speech perception in noise by periodicity 12-15, processing: A neurobiological model and 23,24 Signal processing algorithm", Speech Communication vol. 57, Sep. 25, 2013, pp. 114-125.
Search Report issued Jul. 13, 2022 in GB Application 2115950.4.
Taylor, R. S. et al., "The clinical and cost effectiveness of advances in hearing aid technology: report to the National Institute for Clinical Excellence", In: Database of Abstracts of Reviews of Effects (DARE): Quality-assessed Reviews [Internet] York (UK): Centre for Reviews and Dissemination (UK); 1995-. Available from: https://www.ncbi.nlm.nih.gov/books/NBK68588/, 2 pages (2001).
Verhey, Jesko L. et al., "Effects of sequential streaming on auditory masking using psychoacoustics and auditory evoked potentials", Hearing Research, vol. 285, No. 1-2, pp. 77-85 (Mar. 2012).
Branscombe, Mary, "Beyond the Switchboard: The Current State of the Art in Speech Recognition", retrieved from https://thenewstack.io/speech-recognition-getting-smarterstate-art-speech-recognition/, 10 pages (Nov. 10, 2017).
Warren, Edus H., et al., Effects of contralateral sound on auditory-nerve response, Hear Research, vol. 37, No. 2, pp. 89-104, Jan. 1989.
Wayne, Rachel et al., "A review of causal mechanisms underlying the link between age-related hearing loss and cognitive decline," Ageing Research Review, vol. 23, Pt. B, pp. 154-166, Sep. 2015.
World Health Organization, "Priority Assistive Products List," The Gate Initiative, Feb. 1, 2016.
Winslow, Raimond L. et al., "Single-tone intensity discrimination based on auditor-nerve rate responses in backgrounds, of quiet, noise, and with stimulation of the crossed olivocochlear bundle," Hearing Research, vol. 35, pp. 165-190, Sep. 15, 1988.
Yasin, Ifat et al., "Effect of Human Auditory Efferent Feedback on Cochlear Gain and Compression," The Journal of Neuroscience, vol. 34, No. 46, pp. 15319-15326, Nov. 12, 2014.
Yasin, Ifat et al., "Effect of auditory efferent time-constant duration on speech recognition in noise," The Journal of the Accoustical Society of America, vol. 143, pp. EL112-EL115, Feb. 13, 2018.
Yasin, Ifat et al., "Optimizing Speech Recognition Using a Computational Model of Human Hearing: Effect of Noise Type and Efferent Time Constants," IEEE Access, vol. 8, pp. 56711-56719, Mar. 23, 2020.
Yu, Hong et al., "Spoofing Detection in Automatic Speaker Verification Systems Using DNN Classifiers and Dynamic Acoustic Features," IEEE Transactions on Neural Networks and Learning Systems, vol. 29, No. 10, Oct. 2018.
Zeng, Fan-Gong et al., "Speech Perception in Individuals With Auditory Neuropathy" Journal of Speech, Language, and Hearing Research, vol. 49, pp. 367-380, Apr. 2006.
Archbold, Sue et al., "The Real Cost of Adult Hearing Loss: reducing its impact by increasing access to the latest hearing technologies," The Ear Foundation, pp. 1-24, 2014.
Ault, Shaun V. et al., "On Speech Recognition Algorithms," International Journal of Machine Learning and Computing, vol. 8, No. 6, Dec. 2018.
Backus, Bradford C. et al., "Time-course of the human medial olivocochlear reflex," J. Acoust. Soc. Am., vol. 119, pp. 2889-2904, May 1, 2006.
Blazer, Dan G. et al., "Hearing Health Care for Adults:Priorities for Improving Access and Affordability," National Academies, Sciences Engineering Machine, 2016.
Brown, Guy J. et al., "A computer model of auditory efferent suppression: Implications for the recognition of speech in noise," J. Acoust. Soc. Am., vol. 127, No. 2, Feb. 5, 2010.
Cherry, E. Collin, "Some Experiments on the Recognition of Speech, with One and with Two Ears," J. Acoust. Soc. Am., vol. 25, pp. 975-979, Sep. 1, 1953.
Chintanpalli, Chintanpalli et al., "Modeling the Anti-masking Effects of the Olivocochlear Reflex in Auditory Nerve Responses to Tones in Sustained Noise," Jaro, vol. 13, pp. 219-235, 2012.
Chung, King, "Challenges and Recent Developments in Hearing Aids Part I. Speech Understanding in Noise, Microphone Technologies and Noise Reduction Algorithms," vol. 8, No. 3, pp. 83-124, 2004.
Clark, Nicholas R. et al., "A frequency-selective feedback model of auditory efferent suppression and its implications for the recognition of speech in noise," J. Acoust. Soc. Am., vol. 132, pp. 1535-1541, Sep. 12, 2012.
Cooper, N. P. et al., "Separate mechanical processes underlie fast and slow effects of medial olivocochlear efferent activity," Journal of Physioliology, vol. 548, No. 1, pp. 307-312, 2003.
Dillon, Harvey et al., "The trainable hearing aid: What will it do for clients and clinicians?" The Hearing Journal, vol. 59, No. 4, Apr. 2006.
Van Dijk, Pim et al., "Physiology, Psychoacoustics, and Cognition in Normal and Impaired Hearing," Advances in Experimental Medicine and Biology, vol. 894, 2016.
Ferry, Robert T. et al., "A computer model of medial efferent suppression in the mammalian auditory system," The Journal of the Accoustical Society of America, vol. 122, pp. 3519-3526, Dec. 1, 2007.
Gao, Yayue et al., "Selective Attention Enhances Beta-Bank Cortical Oscillation to Speech under 'Cocktail-Party' Listening Conditions," Frontiers in Human Neuroscience, vol. 11, Article 34, Feb. 2017.
Ghitza, Oded, "Auditory Neural Feedback as a Basis for Speech Processing," AT&T Bell Laboratories, 1988.
Giraud, Anne Lise et al., "Auditory efferents involved in speech-innoise intelligibility," Cognitive Neuroscience and Neuropsychology, Rapid Science Publishers, vol. 8, No. 7, pp. 1779-1783, May 1997.
World Health Organization, "Global Estimates on Prevalence of Hearing Loss," Prevention of Deafness WHO, Jul. 2018.
Guinan, John J. et al., "Medial efferent inhibition produces the largest equivalent attenuations at moderate to high sound levels in cat auditory-nerve fibers," The Journal of the Accoustical Society of America, vol. 100 pp. 1680-1690, Sep. 1, 1996.

(56) References Cited

OTHER PUBLICATIONS

Guinan, John J., "Cochlear efferent innervation and function," Hearing science and vestibular medicine, Otolaryngology & Head and Neck Surgery, vol. 18, pp. 447-453, 2010.
Guinan, John J., "Olivocochlear efferents: Their action, effects, measurement and uses, and the impact of the new conception of cochlear mechanical responses," Hearing Research, vol. 362, pp. 38-47, 2018.
Shield, Bridget, Evaluation of the Social and Economic Costs of Hearing Impairment, A Report for Hear-It, 2006.
Heinz, Michael G. et al., "Auditory nerve model for predicting performance limits of normal and impaired listeners," Accoustic Research Letter Online, ARLO, vol. 2, pp. 91-96, Jul. 1, 2001.
Hedrick, Mark S. et al., "Effects of Physiological Internal Noise on Model Predictions of Concurrent Vowel Identification for Normal-Hearing Listeners," PLOS ONE, Feb. 11, 2016.
Ho, Hao Tam et al., "Auditory Sensitivity and Decision Criteria Oscillate at Different Frequencies Separately for the Two Ears," Current Biology, vol. 27, pp. 3643-3649, Dec. 4, 2017.
"Hearing loss: an important global health concern," The Lancet, vol. 387, p. 2351, Jun. 11, 2016.
Jennings, Skyler G., et al., "The Frequency Selectivity of Gain Reduction Masking: Analysis Using Two Equally-Effective Maskers," The Neurophysiological Bases of Auditory Perception, pp. 47-58, Feb. 16, 2010.
Jennings, Skyler G., et al., "Evaluating the effects of olivocochlear feedback on psychophysical measures of frequency selectivity," J. Acoust. Soc. Am., vol. 132, No. 4, Oct. 2012.
Jãrgens, Tim et al., "The function of the basilar membrane and medial olivocochlear (MOC) reflex mimicked in a hearing aid algorithm," J. Acoust. Soc. Am., vol. 135, Issue 4 Supplement, Apr. 2014.
Jurgens, Tim et al., "Exploration of a physiologically-inspired hearing-aid algorithm using a computer model mimicking impaired hearing," International Journal of Audiology, vol. 55, No. 6, pp. 346-357, Feb. 26, 2016.
Kawase T. et al., "Antimasking Effects of the Olivocochlear Reflex. II. Enhancement of Auditory-Nerve Response to Masked Tones," J Neurophysiol.,m vol. 70, No. 6, pp. 2533-2549, Dec. 1993.
Kuo, Sen M. et al., "Active Noise Control: Open Problems and Challenges," The 2010 International Conference on Green Circuits and Systems, Shanghai, China, pp. 164-169, Jun. 21-23, 2010.
Liberman, M.C. et al., "The ipsilaterally evoked olivocochlear reflex causes rapid adaptation of the 2 f 1-f 2 distortion product otoacoustic emission," The Journal of the Accoustical Society of America, vol. 99, pp. 3572-3584, Jun. 1, 1996.
Lopez-Poveda, Enrique A. et al., "A Binaural Cochlear Implant Sound Coding Strategy Inspired by the Contralateral Medial Olivocochlear Reflex," Ear Hear, vol. 37, No. 3, pp. 138-148, May-Jun. 2016.
Maison, Stephane. et al., "Medial Olivocochlear Efferent System in Humans Studied With Amplitude-Modulated Tones," The American Physiological Society, pp. 1759-1768, vol. 77, No. 4, Apr. 1997.
Maison, S. et al., "Sinusoidal Amplitude Modulation Alters Contralateral Noise Suppression of Evoked Otoacoustic Emissions in Humans," Neuroscience, vol. 91, No. 1, pp. 133-138, 1999.
Martin, Rainer, "Noise Power Spectral Density Estimation Based on Optimal Smoothing and Minimum Statistics," IEEE Transactions on Speech and Audio Processing, vol. 9, No. 5, Jul. 2001.
May, Tobias et al., "Assessment of Broadband SNR Estimation for Hearing Aid Applications," 017 IEEE International Conference on Acoustics, Speech and Signal Processing (ICASSP), New Orleans, LA, USA, , pp. 231-235, 2017.
Meddis, Ray et al., "A computational algorithm for computing nonlinear auditory frequency selectivity," The Journal of the Accoustical Society of America, vol. 109, pp. 2852-2861, Jun. 1, 2001.
Messing, David P., et al., "A non-linear efferent-inspired model of the auditory system; matching human confusions in stationary noise," Speech Communication, vol. 51, Issue 8, pp. 668-683, Aug. 2009.
Poghosyan, Vahe et al., "Attention Modulates Earliest Responses in the Primary Auditory and Visual Cortices," Cell Press, Neuron vol. 58, pp. 802-813, Jun. 12, 2008.
Russell, Ian J., "Medial efferent inhibition suppresses basilar membrane responses to near characteristic frequency tones of moderate to high intensities," The Journal of the Accoustical Society of America, vol. 102, pp. 1734-1738, Sep. 1, 1997.
Report of the Secretary-General, "Progress towards the Sustainable Development Goals," General Assembly, Economic and Social Council, Seventy-ninth session, 2024 session, Item 18 of the preliminary list, Sustainable development, May 2, 2024.
Smalt, Christopher J., et al., "Modeling the Time-Varying and Level-Dependent Effects of the Medial Olivocochlear Reflex in Auditory Nerve Responses," J Assoc Res Otolaryngol., vol. 15, No. 2, pp. 159-173, Apr. 2014.
Strickland, Elizabeth A., et al. "The temporal effect in listeners with mild to moderate cochlear hearing impairment," The Journal of the Accoustical Society of America, vol. 118, pp. 3211-3217, Nov. 1, 2005.
Strickland, Elizabeth A., et al. "The relationship between precursor level and the temporal effect," The Journal of the Accoustical Society of America, vol. 123, pp. 946-954, Feb. 1, 2008.
Taylor, R. S., et al., "Systematic review of the clinical and cost effectiveness of digital hearing aids," British Journal of Audiology, vol. 35, No. 5, pp. 271-288, Oct. 2001.
Feldman, Michael, "UK Commits a Billion Pounds to AI Development," https://www.top500.org/news/uk-commits-a-billion-pounds-to-ai-development/, Apr. 27, 2018.
UNICEF, Supply Annual Report 2018.
Verhey, Jesko L. et al., "Effect of efferent activation on binaural frequency selectivity," Hearing Research, vol. 350, pp. 152-159, Jul. 2017.
Vondrasek, Martin et al., "Methods for Speech SNR estimation: Evaluation Tool and Analysis of VAD Dependency," Radioengineering, vol. 14, No. 1, Apr. 1, 2005.

* cited by examiner

NEURAL-INSPIRED AUDIO SIGNAL PROCESSOR

CROSS-REFERENCE TO RELATED APPLICATIONS

The present application is a U.S. National Phase Application under 35 U.S.C. § 371 of International Application PCT/EP2022/080302, filed on Oct. 28, 2022, which claims the benefit of priority to United Kingdom Patent Application 2115950.4, filed on Nov. 5, 2021, both of which are incorporated herein by reference in their entireties and for all purposes.

FIELD OF THE INVENTION

The present invention relates to an audio-signal processor, and a method performed by that processor, for filtering an audio signal-of-interest from an input audio signal comprising a mixture of the signal-of-interest and background noise.

BACKGROUND OF THE INVENTION

Audio-signal processing, particularly in regard to the audio-signal processing of human speech or voice, plays a central role in ubiquitous active voice-control and recognition. These are areas representing a rapidly increasing market sector with more and more searches now made by voice.

Audio-signal processing of speech requires devices to have an ability to extract clear speech from ongoing background noise. A sector receiving focus in this respect is next-generation speech processors for hearing assistive devices. Worldwide, disabling deafness affects 1.1 billion people, eighty-seven percent of whom live in the developing world (World Health Organisation (WHO), 2012). Hearing aids are ranked in the top 20 of the WHO Priority Assistive Products List. The Assistive Products List supports the UN Convention on the Rights of Persons with Disabilities to ensure the goal of global access to affordable assistive technology (WHO Priority Assistive Products List, 2016). A major factor contributing to elevated healthcare cost is the non-use of current hearing assistive devices by more than 60% of the hearing-impaired population issued with devices.

The main reason for the non-use of hearing assistive devices is cited to be poor speech enhancement in the presence of background noise (Taylor and Paisley, 2000). The long-term consequences of non-use of issued hearing assistive devices have been shown to be associated with cognitive decline and dementia (Wayne and Johnsrude, 2015). Therefore, improving speech enhancement in background noise is relevant for the design of signal/speech processors used in a range of both non-healthcare (e.g. phones, audio, voice/speech-activated systems/devices, enhanced listening, sound systems, speech recognition, speech-to-text systems, sonics) and healthcare devices (e.g. hearing aids, cochlear implants).

Speech recognition in ongoing background noise still remains a challenge for signal/speech audio-signal processors, which often exhibit sub-optimal performance, especially if focussing on a single-speaker's voice amongst a background of similar speakers (Kuo et al., 2010). Insight into how signal-processing strategies could be improved can be gained from physiological processes that operate in a normal hearing system to improve speech perception in noise.

It is known in the art that prior art signal processors perform sub-optimally in multi-speaker environments (Ault et al., 2018), whereas the human auditory brain performs incredibly well in such environments to enhance speech in ongoing background noise, known as the "cocktail party effect" (Cherry, 1953). For this reason, there is a need for improved audio-signal processors for filtering an audio signal-of-interest (e.g. a speech signals) from an input audio signal comprising a mixture of the signal-of-interest and background noise.

Over the past 20 years, advances in physiological and psychophysical methods have played an important role in understanding the biological systems underlying speech perception in noise. In particular mapping some of the neural mammalian pathways involved in signal (including speech) enhancement in noise (Warren and Liberman, 1989; Winslow and Sachs, 1988). It is now known that descending (efferent) neural fibres from higher-levels of the auditory system can modify auditory processing at lower-levels of the auditory system to enhance speech understanding in noisy backgrounds (Kawase et al., 1993). One such neural pathway, originating in the auditory brainstem (known as Brainstem-mediated, or "BrM" neural feedback) extending from the Superior Olivary Complex by way of the Medial Olivo-Cochlear (MOC) reflex, has been shown to modify the inner ear's response to sound (Liberman et al., 1996; Murugasu and Russell, 1997). A major benefit attributed to this neural feedback in humans is the improvement in detecting the signal of interest (e.g., speech) in noisy environments (Giraud et al., 1997), as evidenced by human neural-lesion studies (Giraud et al., 1997; Zeng and Liu, 2006). Other descending neural pathways from the auditory cortex (e.g. Cortical-mediated, or "CrM" neural feedback), involve attentional neural pathways which can further modify lower-level sound processing to enhance speech understanding in noise (Gao et al., 2017; Lauzon, 2017).

Human cortical brain activity, associated with attentional oscillations is known to influence speech perception in noise (Gao et al., 2017) by affecting lower-level neural feedback to the ear's response to sound (Lauzon, 2017). However, so far these effects have not been successfully incorporated in signal processors because the appropriate correspondence between oscillatory changes in auditory attention and features of the incoming stimulus had not been identified. This has recently been resolved by studies in the fields of vision and audition, using electroencephalography (EEG) and psychophysics (Yu et al., 2017; Ho et al., 2017). In vision, attentional oscillations have been shown to affect detection performance by up to 10% (Ho et al., 2017). In current auditory models, effects of human cortical attentional oscillations on perception are modelled as deterministic (a fixed decrement in performance), or random (internal noise) (Hedrick, 2016). As with vision, auditory discriminability and criterion demonstrate strong cortical oscillations in different frequency ranges of cortical activity: ~6 Hz for sensitivity and ~8 Hz for criterion (Yu et al., 2017; Ho et al., 2017) with both affecting signal detection/classification. Incorporating oscillatory phase data into the decision device of an auditory signal processor to enhance speech is expected to improve speech detection by a similar degree and has to date, not been considered in speech processor design.

However, knowledge of descending neural pathways (e.g. BrM and CrM neural feedback) has also been obtained predominantly from physiological studies on small non-human mammals. A known problem in the prior art has always been to design appropriate methodologies to measure the effect of this neural feedback on human hearing. Since the 2000's, psychophysical (e.g., Strickland and Krishnan (2005); Strickland (2008); Jennings and Strickland (2010;

2012); Yasin et al., 2014) and otoacoustic emission measures (Backus and Guinan, 2006) have been used to infer the effect of BrM neural feedback on auditory processing in humans. Some of this human-derived data has been used for computational modelling of the auditory system, albeit using a restricted human dataset.

A few computational models of the human auditory system (that also underlie some signal-processing strategies) have used aspects of BrM neural feedback to improve speech in background noise (Ghitza 1988; Ferry and Meddis, 2007), or have modelled how such bio-inspired feedback improves tonal sound discrimination in noise (Chintapalli et al., 2012; Smalt et al., 2014). However, these models are based on small non-human mammalian datasets and simulate the physiological and neural processes in such mammals, such that they are not optimised for human applications.

Previous auditory computational models (Ferry and Meddis, 2007; Brown et al., 2010, Clark et al., 2012 Ghitza, 1988; Messing et al., 2009; Lopez-Poveda, 2017) do implement aspects of simulated BrM neural feedback for signal-processor design, but are limited in their effectiveness in enhancing speech in noise. This is due to their use of BrM neural feedback parameters often modelled using small mammalian datasets).

In known prior art devices, for instance hearing assistive devices have incorporated surface electrodes (US 2013101128A), or are partly implanted (US2014098981A), to record bio-signals from the skin surface (electroencephalography; EEG), combined in some cases with feature extraction, (with a feedback signal re-routed from an output action, rather than based on BrM neural inspired feedback) (US2019370650A) but this has not incorporated any of the other components in the combinations described for an audio-signal processor.

It is with these problems in mind that the inventors have devised the present invention to overcome the shortcomings of the prior art.

SUMMARY OF THE INVENTION

Accordingly, the present invention aims to solve the above problems by providing, according to a first aspect, an audio-signal processor for filtering an audio signal-of-interest from an input audio signal comprising a mixture of the signal-of-interest and background noise, the processor comprising a frontend unit, the frontend unit comprising a filterbank comprised of an array of bandpass filters, a sound level estimator, and a memory with one or more input-output, I/O, functions stored on said memory; wherein the frontend unit is configured to receive:

an unfiltered input audio signal, and human-derived neural-inspired feedback signals (NIFS).

wherein the frontend unit is further configured to:

extract sound level estimates from an output of the one or more bandpass filters using the sound level estimator, modify the input-output, I/O, functions in response to the received sound level estimates and the NIFS, and determine enhanced I/O functions, and store the enhanced I/O functions on the memory and use the enhanced I/O functions to determine one or more modified filterbank parameters in response to the received NIFS and sound level estimates, apply the modified filterbank parameters either across one filter of the filterbank or across a range of filters of the filterbank within the frontend unit, and output a filtered audio signal to a sound feature onset detector for further processing.

Filterbanks include an array (or "bank") of overlapping bandpass filters which include the one or more bandpass filters. The audio-signal processor includes a 'front-end unit' with a filterbank. The filterbank response is "tuned" to the neural feedback (i.e., NIFS) based on human data. To accomplish this, across-filter tuning of the feedback is based on previous published (Yasin et al., 2014; Drga et al., 2016) and unpublished human psychophysical and physiological data. For example, aspects of the NIFS may be based on the published and unpublished data from humans used to depict the change of the full I/O function in response to neural feedback activated by unmodulated and modulated sounds.

In preferred embodiments, the NIFS may be parameters derived from brain recordings (e.g. direct ongoing, pre-recorded, or generic human-derived datasets) and/or measurements derived by psychophysical/physiological assessments (e.g. direct ongoing, pre-recorded, or generic human-derived datasets). The NIFS may be processed by a higher-level auditory information processing module in conjunction with information received from a sound feature onset detector module and a signal to noise ratio estimator module at the output of the frontend unit.

The processor's 'front-end unit' includes the filterbank. The filterbank comprises an array of overlapping bandpass filters covering (for instance in a hearing aid) the range of frequencies important for speech perception and music. A gain and input-output (I/O) level function for a given filter and/or range of filters is set as follows depending on the input.

I/O functions can be represented graphically showing how an output signal level (e.g. of a hearing aid) varies at various input signal levels. In this way, as is also known in the art, I/O functions can be used to determine the gain (in decibels), G (i.e. gain (G)=output (O)−input (I)) with respect to a given input (I) signal level. The I/O function can also be used to determine a change in gain (ΔG) with respect to a given input (I) signal level. Sometimes, the change in gain (ΔG) is referred to as "compression". The I/O function may be derived from published and unpublished human data sets using both modulated noise (of varying types) and unmodulated noise (e.g., Yasin et al., 2020). The filterbank output (such as the sound level estimates) are used to modify the I/O function stored (e.g. on a memory) and determines an "enhanced" I/O function. As the I/O function is modified it becomes, as the names suggest, more honed or improved ("enhanced") for purpose over time.

In one embodiment, the one or more I/O functions stored on the memory maybe human-derived I/O functions. In this example, the frontend unit is configured to modify the human-derived I/O functions in response to the received sound level estimates and the NIFS and determine an enhanced I/O functions.

In other preferred embodiments, elements of processed information are used in conjunction with information derived from the output of a feature extraction module in order to feed into a machine learning unit. In some embodiments, the machine learning unit has an internal decision device that interacts with the higher-level auditory information processing module in order to further optimise the NIFS parameters and optimise speech enhancement in background noise in the resultant output speech-enhanced filtered output audio signal.

Enhanced I/O functions may specify how the functions are affected by sound level estimates as well as by neural feedback (e.g. BrM and CrM feedback and feedback from other higher levels of the auditory system) depending on the input level and temporal parameters of the sound input. In this way, incoming speech and background noise mixture is processed by an "enhanced" filterbank where a number of filter attributes can be adapted by neural-inspired feedback within the processor.

The processor of the present application advantageously incorporates human-derived neural-inspired feedback signals (NIFS) into an audio-signal processor. NIFS refer to aspects of neural feedback that are uniquely used by the human brain during the human brain's biological signal-processing of sound. The NIFS may, in some uses of the audio-processor refer to parameters derived from direct ongoing recordings of brain activity (e.g., such as being received from EEG), or use pre-recorded or generic human-derived datasets relating to brain activity recordings from humans. In other cases the NIFS may be derived from previous published (Yasin et al., 2014; Drga et al., 2016) and unpublished human psychophysical and physiological data (generic human-derived datasets), or have been derived by psychophysical/physiological assessments conducted on the user (direct ongoing or pre-recorded).

The audio-signal processor of the present application may be used to perform the function of filtering an audio signal-of-interest (e.g. a speech signal) from an input audio signal comprising a mixture of the signal-of-interest and background noise. For this reason, the claimed processor can be used in various hearing assistive devices, such as hearing aids or cochlear implants, for example. In other words, the processor of the present invention uses a biomimicry of the human's auditory system in order to emulate the human brain's improved ability for audio-signal filtering, and therefore provides an improved audio-signal processor over known prior art audio-signal processors and/or signal-processing strategies.

By using NIFS, the claimed audio-signal processor of the present invention may be thought of as a "Neural-Inspired Intelligent Audio Signal" or "NIIAS" processor, where the input data is processed using parameters that are biologically inspired (bio-inspired) from humans.

These parameters could be derived from direct ongoing recordings of brain activity (e.g., such as being received from EEG), or use pre-recorded or generic human-derived datasets relating to brain activity recordings from humans. In other cases the NIFS may be derived from previous published (Yasin et al., 2014; Drga et al., 2016) and unpublished human psychophysical and physiological data (generic human-derived datasets), or have been derived by psychophysical/physiological assessments conducted on the user (direct ongoing or pre-recorded). The claimed audio-signal processor may be thought of as Neural-Inspired Intelligent Audio Signal, as these parameters are improved or optimised for the user by way of the machine learning unit.

The processor of the present application provides improved speech in (background) noise performance when compared to other audio signal processors by using a strategy based on a human-derived neural feedback mechanisms that operates in real time to improve speech in noisy backgrounds.

Optionally, the claimed processor can be integrated into a variety of speech recognition systems and speech-to-text systems. In this way, the claimed processor may also be referred to as a "NIIAS Processor Speech Recognition" or a "NIIASP-SR". Example applications of the claimed processor may be for use in systems where clear extraction of speech against varying background noise is required. Examples of such applications include but are not limited to automated speech-recognition software and/or transcription software such as Dragon Naturally Speaking, mobile phone signal processors and networks, such as Microsoft™ speech-recognition, Amazon's Alexa™, Google Assistant™, Siri™ etc.

Optionally, the claimed processor may be used as a component for cochlear implants. In this way, the claimed processor may be referred to as a "NIIAS Processor Brain Interface Cochlear Implant" or a "NIIASP-BICI". In this example application, the claimed processor may be integrated within the external unit speech processor unit of a continuous integration (CI) with surface electrodes. The surface electrodes may be used to provide an electrode input for the claimed processor. The surface electrodes may be located within the ear canal of a user in order to record ongoing brain activity and customise operation to the user. The claimed processor and combined electrode input may be used to modulate current flow to the electrodes surgically implanted within the cochlea of the inner ear. Potentially, a device utilising the claimed processor would be purchased by the private health sector and the NHS.

Optionally, the claimed processor may also be used within the wider field of robotics systems. In this way, the claimed processor may be referred to as a "NIIAS processor Robotics" or a "NIIASP-RB". In this example application, the claimed processor model can also be incorporated into more advanced intelligent systems design that can use the incoming improved speech recognition as a front-end for language acquisition and learning and more higher-level cognitive processing of meaning and emotion.

Optionally, the claimed processor may also be used as an attentional focussing device. In this way, the claimed processor may also be referred to as a "NIIAS Processor Attention" or a "NIIASP-ATT". In this example application, the claimed processor in-the-ear model with surface electrodes can also be combined with additional visual pupillometry responses to capture both audio and visual attentional modulation. Attentional changes captured by visual processing can be used to influence the audio event detection, and vice-versa. Such a device, utilising the claimed processor, can be used by individuals to enhance attentional focus (this could possibly include populations with attention-defect disorders, or areas of work in which enhanced attention/sustained attention is required) and aspects of such a system could also be used by individuals with impaired hearing.

Further optional features of the invention will now be set out. These are applicable singly or in any combination with any aspect of the invention.

In use, incoming speech and background noise mixture is processed by the frontend unit including the filterbank and a number of parameters can be modified in response to the received NIFS within the processor.

Optionally, the one or more modified parameters may include: i) a modified gain value and ii) a modified compression value for a given input audio signal, and wherein the frontend unit may be further configured to: apply the modified gain value and the modified compression value to the unfiltered input audio signal by way of modifying the input or parameters of a given filter or range of filters of the filterbank to determine a filtered output audio signal.

A few prior art models have used very limited data relating to neural-inspired feedback, in particular, BrM feedback from humans (e.g. a single time constant). However, all prior art models have used that information in a limited way. For example, in prior art models the effects of the neural-inspired feedback is not configured to be tuned across auditory filters, and have used a limited range of time-constants, and do not apply the neural-inspired feedback to modify an I/O function of I/O functions, the front-end gain, and the compression within and across auditory filters during the time-course of sound stimulation.

Optionally, the claimed processor may be used within a hearing aid device. In this way, a hearing aid device using the claimed processor may also be referred to as a "NIIAS processor Hearing Aid" or a "NIIASP-HA". For example, the processor can be housed in an external casing, existing outside of the ear or an in-the-ear device, such as within the concha or ear canal. Alternatively, or additionally, the hearing aid device may operate as a behind-the-ear device, accessible and usable by a substantial proportion of the hearing-impaired user market and purchased via private health sector as well as independent hearing-device dispensers and purchased by the NHS. In this way, the architecture of the claimed processor can also be used to design cost-effective hearing aids (e.g. by using 3-D printed casings) coupled to mobile phones (to conduct some of the audio-processing) for the hearing-impaired (i.e. referred to as a "NIIASP-HA-Mobile"). In this embodiment, most of the complex audio-processing can be conducted by a smartphone connected by a wireless connection (e.g. Bluetooth™) to the behind-the-ear hearing aid.

Optionally, the audio-signal processor may further comprise: a Higher-Level Auditory Information (HLAI) processing module, comprising an internal memory. The HLAI processing module may be configured to receive human-derived brain-processing information (e.g. such as parameters derived either directly from brain recordings; e.g. ongoing brain recordings) via recordings from surface electrodes or indirectly via pre-recorded or generic human-derived datasets relating to brain activity recordings from humans and/or measurements derived by psychophysical/physiological assessments [e.g. direct ongoing, pre-recorded, or generic human-derived datasets such as from previous published (Yasin et al., 2014; Drga et al., 2016) and unpublished human psychophysical and physiological data], and store it on its internal memory and, using said brain-processing information, the HLAI may be further configured to simulate aspects of the following, which constitute aspects of the NIFS:

- brainstem-mediated, BrM, neural feedback information and
- cortical-mediated, CrM, neural feedback information (e.g. including information relating to attention).

Prior-art auditory models have used aspects of BrM neural-inspired feedback based on information derived from small non-human mammalian datasets, rather than derived from humans.

Optionally, the HLAI processing module may be further configured to derive the human-derived NIFS using said simulated and/or direct BrM and/or CrM neural feedback information and relay said NIFS to the frontend unit.

Optionally, the HLAI processing module may be configured to receive the brain-processing information by direct means or by indirect means from higher-levels of auditory processing areas of a human brain, and wherein the brain-processing information may be derived from any one of, or a combination of, the following: psychophysical data, physiological data, electrophysiological data, or electroencephalographic (EEG) data.

Optionally, the human-derived brain-processing information may further comprise a range of time constants which define an exponential build-up and a decay of gain with time derived from human-derived measurements; and wherein HLAI processing module may be further configured to modify the human-derived NIFS using said time constants in response to the received brain-processing information and relay said NIFS to the frontend unit. The range of time constants can be measured psychophysically from humans. For instance, the inventors have developed a method by which such time constants can be measured from humans and have measured time constants ranging from 110 to 140 ms in humans. In simulating speech recognition effects using an ASR system the inventors have shown a beneficial effect of a range of time constants having any value between 50 to 2000 ms (Yasin et al 2020).

In some embodiments of the audio-signal processor, the range of time constants defining the build-up and decay of gain $\tau_{on}$ and $\tau_{off}$ respectively, may extend to any value below 100 ms. For example, the time constants may lie within a range that is a contiguous subset of values lying from 0 (or more) to 100 ms (or less). For example, the range of time constants may be any value between 5 to 95 ms, for example any value between 10 to 90 ms. The range of time constants may be any value between 15 to 85 ms, such as any value between 20 to 80 ms, for example any value between 25 to 75 ms. The range of time constants may be any value between 30 to 70 ms, such as any value between 35 to 65 ms, for example any value between 40 to 60 ms. The range of time constants may be any value between 45 and 55 ms, for example being values such as 46 ms, 47 ms, 48 ms, 49 ms, 50 ms, 51 ms, 52 ms, 53 ms, and/or 54 ms.

In other embodiments, the range of time constants could be any value between 50 to 2000 ms. For example, the time constants may lie within a range that is a contiguous subset of values lying from 50 (or more) to 2000 ms (or less). In other embodiments of the audio-signal processor, the range of time constants may be any value between 90 to 1900 ms, such as any value between 100 to 1800 ms, for example 110 to 1700 ms. The range of time constants may be any value between 120 to 1600 ms, such as any value between 130 to 1500 ms, for example 140 to 1400 ms. The range of time constants may be any value between 150 to 1300 ms, such as any value between 160 to 1200 ms, for example 170 to 1100 ms. The range of time constants may be any value between 180 to 1000 ms, such as any value between 190 to 900 ms, for example 200 to 800 ms. The range of time constants may be any value between 210 to 700 ms, such as any value between 220 to 600 ms, for example 230 to 500 ms. The range of time constants may be any value between 240 to 400 ms, such as any value between 250 to 300 ms.

The enhanced I/O functions (for a range of signal levels and temporal relations), from which gain is estimated, may describe the change in output with respect to the input (and therefore the gain at any given input), also the change in gain with input, which defines the compression, and the build-up and decay of gain. The build-up and decay of gain may be specified by time constants of $\tau_{on}$ and $\tau_{off}$ respectively, which are also derived from human auditory perception studies involving BrM neural feedback effects (published Yasin et al., (2014) and unpublished data) which define the filter gain build-up and decay in gain effects.

Optionally, the range of time constants may comprise human-derived onset time build-up constants, $\tau_{on}$, applied to the I/O function(s) stored in the frontend unit to modify the I/O function(s) and derive the enhanced I/O function(s) stored in the front end to modify the rate of increase of the gain value, the effects of which are subsequently applied to the filter or filters of the filterbank.

In some embodiments, the onset time build-up constants $\tau_{on}$ maybe derived from human data relating to both steady-state and modulated noise. In other embodiments, the onset time build-up constants $\tau_{on}$ maybe any time-value constant which is not necessarily human-derived.

In this way, $\tau_{on}$ can be considered to be a "build-up of gain" time constant.

Optionally, the range of time constants may comprise human-derived offset time decay constants, $\tau_{off}$, applied to the I/O functions stored in the frontend unit to modify the I/O functions and derive the enhanced I/O functions stored in the front end to modify the rate of decrease of the gain value, the effects of which are subsequently applied to the filter or filters of the filterbank. In some embodiments, the offset time decay constants $\tau_{off}$ are derived from human data relating to both steady-state and modulated noise. In other embodiments, the offset time decay constants off maybe any time-value constant which is not necessarily human-derived.

In this way, $\tau_{off}$ can be considered to be a "decay of gain" time constant.

There may be a continuum of gain values derived from human datasets, dependent on input sound aspects such as level, and temporal characteristics which define the filter gain applied.

In some embodiments, the modified gain values may be a continuum of gain values, derived from human data that may be in the following range: 10 to 60 dB. In some embodiments, the gain values are derived from human data relating to both steady-state and modulated noise.

Optionally, the modified gain values may be a continuum of gain values that have a values anywhere from 0 to 60 dB, depending on the external averaged sound level (as processed via the filterbank) and current instantaneous sound level. In other embodiments, the continuum of gain values maybe any continuum of numerical gain values which are not necessarily human-derived.

Optionally, the modified gain values are a continuum of gain values that may have a value of 10 dB or more, 15 dB or more, 20 dB or more, 25 dB or more or 30 dB or more; and may have a value of 60 dB or less, 55 dB or less, 50 dB or less, 45 dB or less, or 40 dB or less. The continuum of gain values may have a total range of 10 to 60 dB or the continuum of gain values may cover a range of: 15 to 55 dB, a range of 20 to 50 dB, or a range of 25 to 45 dB. The continuum of gain values may have a range of 30 to 40 dB, for example a value of 35 dB would fit within the range.

In some embodiments, the modified gain values may be any value greater than 60 dB, such as being a continuum of gain values that fall within a range and where the upper and lower boundaries of that range are greater than 60 dB.

The gain may be obtained from a continuum of gain values derived from enhanced I/O functions inferred from simulation studies using unmodulated and modulated sounds (with a range of signal levels and temporal settings) from Yasin et al. (2020), secondary unpublished data analyses based on data from Yasin et al. (2014), and unpublished human data using unmodulated and modulated signals.

There may be a continuum of compression estimates (the change in gain) also derived from human datasets, dependent on input sound aspects such as level, wherein input sound aspects comprise a sound level and temporal characteristics which define the compression applied. In contrast, other current models use a "broken-stick" function to apply compression, providing a limited range of compression values (e.g. Ferry and Meddis, 2007), In some embodiments of the audio-signal processor, the modified compression values may be a continuum of compression values that may be in the following range: 0.1 to 1.0. In some embodiments, the compression values are derived from human data relating to both steady-state, unmodulated, and modulated signals.

In other embodiments of the audio-signal processor, the continuum of compression values may include any compression value between 0.15 to 0.95 inclusive, any value between 0.20 to 0.90 inclusive, or any value between 0.25 to 0.85 inclusive. The continuum of compression values may cover values within the range of 0.25 to 0.80 inclusive, such as any value between 0.30 to 0.75 inclusive, for example 0.35 to 0.70 inclusive. The continuum of compression values may include any value between 0.40 to 0.65 inclusive, such as any value between 0.45 to 0.60 inclusive, for example 0.50 to 0.65 inclusive. The continuum of compression values may include any value between 0.55 to 0.60.

Optionally, the filter or filters of the filterbank within the frontend unit may be further configured so as to modify a bandwidth of each of the one or more bandpass filters.

In this way, the applied gain (and thereby effect of any neural-inspired feedback) may be applied per filter (channel) as well as across filters (e.g., Drga et al., 2016).

Optionally, the modified gain and compression values may be:

- either applied to the input audio signal per bandpass filter in the one or more bandpass filters,
- or are applied to the input audio signal across some or all bandpass filters in the one or more bandpass filters.

Optionally, the audio-signal processor further comprises a sound feature onset detector configured to receive the filtered output audio signal from the frontend unit (e.g. where front end unit houses the filterbank, the internal memory, and the sound level estimator) and detect sound feature onsets, and wherein the sound feature onset detector may be further configured to relay the sound feature onsets to the HLAI processing module, and the HLAI processing module may be configured to store said sound feature onsets on its internal memory for determining the NIFS.

Optionally, the sound feature onset detector may be further configured to relay the filtered output audio signal to the HLAI processing module and the HLAI processing module configured to store the filtered output audio signal on its internal memory.

Optionally, the audio-signal processor may further comprise a signal-to-noise ratio, SNR, estimator module configured to receive the filtered output audio signal from the frontend unit and determine a SNR of the mixture of the signal-of-interest and the background noise, and wherein the SNR estimator module may be further configured to relay the SNR to the HLAI processing module, and the HLAI processing module may be configured to store said SNR on its memory for determining the NIFS. In this way, the SNR estimator module uses a changing temporal window to determine an ongoing estimate of the signal-to-noise ratio (SNR) values of the filtered output signal from the frontend unit.

Optionally, the audio-signal processor further comprises a machine learning unit comprising a decision device in data communication with the HLAI processing module, the decision device comprising an internal memory, the decision device may be configured to receive data from the HLAI processing module and store it on its internal memory, wherein the decision device may be configured to process the data and output a speech-enhanced filtered output audio signal.

Optionally, the HLAI and the decision device may utilise pre-recoded generic human data in conjunction with the machine learning unit (also known as a "deep learning component"). For this reason, this embodiment may not have the degree of customisation and individualisation for use in a stand-alone hearing aid (as previously described). This embodiment of the processor may at least be able to access a substantial population and link-up with healthcare providers in the developing world in order to provide a long-term ongoing provision, with minimal upkeep.

However, as digital healthcare evolves, a hearing aid device using the claimed processor may be able to operate as a customised stand-alone device (using either directly recorded information and/or pre-recorded information) remotely adapted by a centralised healthcare system. For example, distributing the audio-processing between a smartphone and hearing aid may be able to reduce overall cost to the user and make the system more accessible to a much larger population. Advantageously, the development of a core auditory model of the claimed processor with improved speech recognition in noise can be incorporated into cost-effective hearing assistive devices linked to mobile phones in order to provide much of the developed, and developing world, with robust and adaptable hearing devices.

The machine learning unit may also be referred to as a "Semi-Supervised Deep Neural Network" or a "SSDNN". The claimed processor may use the neural feedback information (derived from any one of or a combination of the following: psychophysical data, physiological data, electrophysiological data, or electroencephalographic (EEG) data) from both the human brainstem and/or cortex (e.g. including attentional oscillations), in association with incoming sound feature extraction combined with sound feature onset detection information in order to inform both the NIFS and the decision device using the SSDNN, with capacity to learn and improve speech recognition capability over time, with ability to be customised to the individual through a combination of SSDNN and further direct/indirect recordings.

When comparing the novel architecture of the (NIIAS) audio-signal processor with known audio processors/devices it is evident that, although they may include one or more of the elementary characteristic processing stages, they do not combine the processing in the way described or include other key components of the architecture such as BrM neural feedback connected with the CrM neural processing component, the SNR extraction combined with the feature extraction, the decision device as embedded within the SSDNN architecture and connected with the CrM neural processing component to enhance speech in noise.

Optionally, the audio-signal processor may further comprise a feature extraction, FE, module, said FE module may be further configured to perform feature extraction on the filtered output audio signal, and the FE module may be further configured to relay the extracted features to the machine learning unit, and the decision device is configured to store the extracted features in its internal memory.

Optionally, the claimed processor can be housed in a casing embedded with surface electrodes to make contact with the ear canal or outer concha area to record activity from the brain. In this way, the claimed processor may also be referred to as a "NIIAS Processor Ear-Brain Interface" or "NIIASP-EBI". In this example application, surface electrodes record ongoing brain activity and customise operation to the user. In this example application, the HLAI component and decision device can use direct brain activity in conjunction with the machine learning unit, to customise the device to the users' requirements. The device can be used by normal-hearing individuals as an auditory enhancement device, for focussing attention, or by hearing impaired as an additional component to the hearing aids described earlier. Such a device can be purchased commercially (e.g. as an auditory/attentional enhancement device) or health sector/independent hearing-device dispensers (e.g. as a hearing aid).

Optionally, the SNR estimator module may be configured to relay the filtered output audio signal with the SNR estimation values to the FE module, the FE module is configured to relay the filtered output audio signal to the machine learning unit, and the decision device is configured to store the filtered output audio signal in its internal memory.

Optionally, the decision device may be configured to process:

the data received from the HLAI processing module, which includes the SNR values, and the extracted features, sound feature onsets and attentional oscillations data that can be used to improve detection, and outputs a speech-enhanced filtered output audio signal.

Optionally, the machine learning unit further comprises a machine learning algorithm stored on its internal memory, and wherein the decision device applies an output of the algorithm to the data received from the HLAI processing module, including the SNR values, the extracted features, and derives neural-inspired feedback parameters.

Optionally, the machine learning algorithm may encompass a combination of both supervised and unsupervised learning using distributed embedded learning frames. In other embodiments, the machine learning algorithm may use feature extraction information and the input from the SNR estimator module to learn dependencies between the signal and feature extraction, using input from the HLAI to predict optimal HLAI and subsequently NIFS values over time.

Optionally, the claimed processor may also be used as a brain-ear interface, designed as part of an in-the-ear device for enhanced audio experience when using virtual reality displays/systems. In this way, the claimed processor may also be referred to as "NIIAS Processor Virtual/Augmented Reality" or "NIIASP-VAR". In this example application, the claimed processor may be incorporated into device in electronic communication with surface electrodes within the ear of a user in order to record ongoing brain EEG signals for monitoring attention shifts due to ongoing audio and visual input for enhanced user experience in virtual reality/augmented reality environments. For instance, the processor can be used to direct the user towards augmented/virtual reality scene/events based on prior or ongoing brain behaviour and enhance attentional focus. Such pre-attentional activity can be used as additional parameters for the machine learning algorithm to predict user audio-visual and attentional behaviour in VR/AR environments.

Optionally, the derived neural-inspired feedback parameters may be relayed, from the decision device, to the HLAI processing module and the HLAI processing module may be configured to store said neural-inspired feedback parameters on its memory for determining the NIFS. In other words, the HLAI processing module can use information from the machine learning unit, higher-level brain processing data (i.e. BrM and CrM feedback data), sound feature onsets, and SNR data, in order to optimise the parameters of the NIFS sent to be applied at the level of the filterbank.

In this way, incoming speech and background noise mixture is processed by the enhanced filterbank unit, with a number of attributes that can be adapted by neural-inspired feedback within the processor, such as filter gain, the change in gain with respect to the input (compression), the build-up and decay of gain ($\tau_{on}$ and $\tau_{off}$) and the filter tuning (associated with the change in gain). The input sound level may also be estimated per and across filter channel(s)

In this way, the audio-signal processor of the present application may be used as a core processor for the previously discussed variety of uses listed here.

According to a second aspect, there is provided a method of filtering an audio signal-of-interest from an input audio signal comprising a mixture of the signal-of-interest and background noise, the method performed by a processor comprising a frontend unit. The frontend unit comprising a filterbank, the filterbank comprising one or more bandpass filters, a sound level estimator, and a memory with an input-output, I/O, function(s) stored on said memory, wherein the filterbank is configured to perform the following method steps:

i) receiving:
  an unfiltered input audio signal,
  human-derived neural-inspired feedback signals, NIFS, and
ii) extracting sound level estimates from an output of the one or more bandpass filters using the sound level estimator,
iii) modifying the input-output, I/O, functions in response to the received sound level estimates and the NIFS, and
iv) determining an enhanced I/O function,
v) storing the enhanced I/O function on said memory, and
vi) using the enhanced I/O function to determine one or more modified parameters to apply to the filter/filters of the filterbank in response to the received NIFS.

Optionally, the one or more modified parameters include: a modified gain value and a modified compression value for a given input audio signal, and wherein the filterbank is further configured to perform the following method steps:

vii) applying the modified gain value and the modified compression value to the unfiltered input audio signal, and viii) determining a filtered output audio signal.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
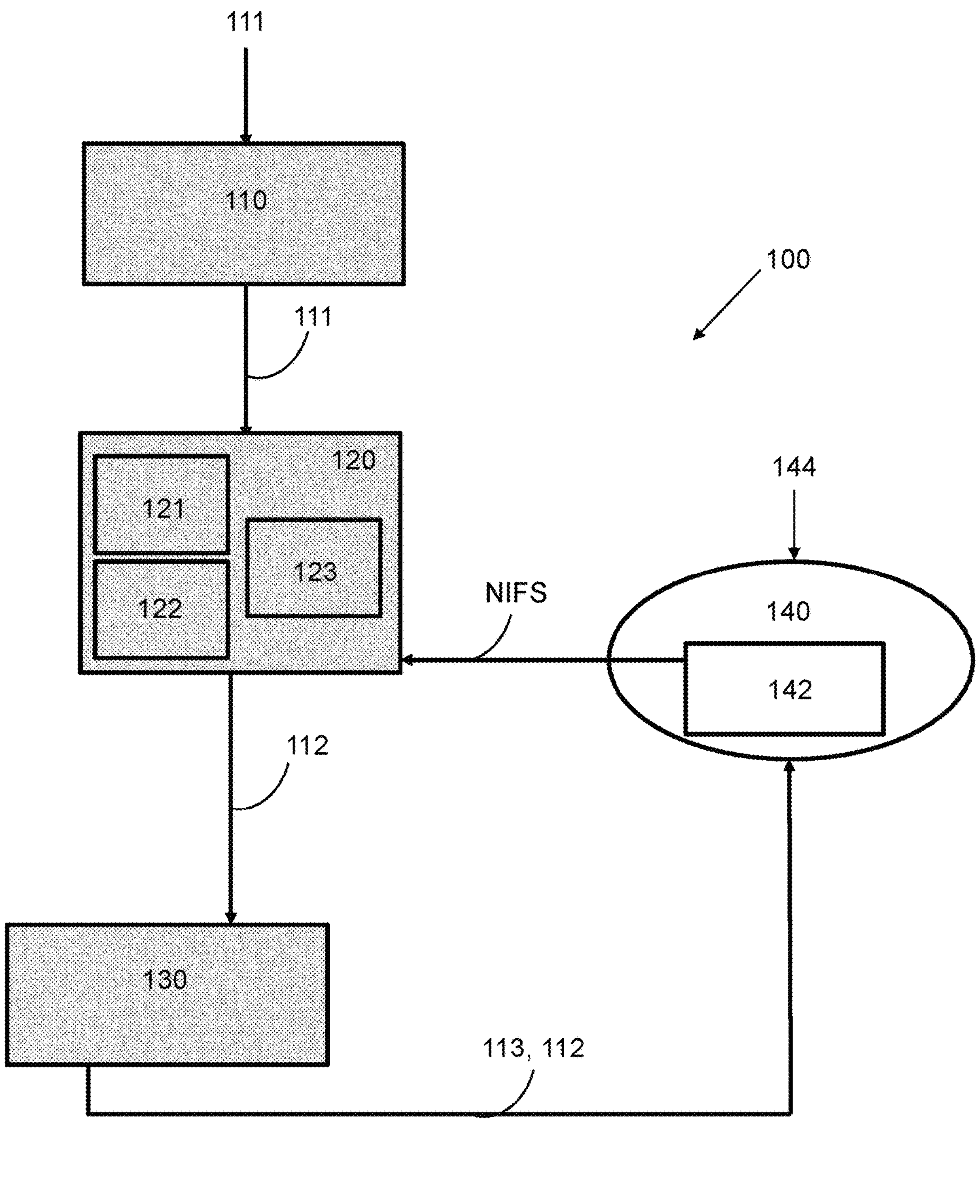
FIG. 1 shows a block diagram of an audio-signal processor according to an embodiment.

FIG. 1 is a block diagram of an audio-signal processor 100 according to an embodiment of the invention. The audio-signal processor 100 shown in FIG. 1 is also referred to as a Neural-Inspired Intelligent Audio Signal (NIIAS) processor. The audio-signal processor 100 includes a receiving unit 110, a frontend unit (120), a Sound Feature Onset Detector (SFOD) 130, and a Higher-Level Auditory Information (HLAI) processing module 140. The receiving unit 110, the frontend unit 120 and the Sound Feature Onset Detector (SFOD) 130 are all associated with front-end audio processing. The HLAI processing module 140 is associated with brain-inspired processing, incorporating HLAI and decision making.

The frontend 120 and the HLAI processing module 140 may take the form of sub-processors that are part of the same audio-signal processor 100. In the embodiment shown in FIG. 1, the receiving unit 110, the frontend 120, the SFOD 130, and the HLAI processing module 140 are all in data communication with each other through wired connections as indicated by the arrows shown in FIG. 1. The receiving unit 110 is in data communication with the frontend unit 120, the frontend 120 is in data communication with the SFOD 130, the SFOD is in data communication with the HLAI processing module 140, and the HLAI processing module 140 is in data communication with frontend unit 120. To illustrate this embodiment, all the components may be part of a printed circuit board (PCB) that forms the audio-signal processor 100. As would be understood by the skilled person, in other embodiments (not shown in the figures), one or more of the components shown in FIG. 1 may instead be in a wireless data communication with each other using known wireless communication protocols (e.g. Wi-Fi, Bluetooth™, etc).

The receiving unit 110 is any device that converts sound into an electrical signal, such as an audio microphone or a transducer as are known in the art. As is also known in the art, the filterbank 121 includes one or more bandpass filters (not shown in the figures). For example, the one or more bandpass filters are an array (or "bank") of overlapping bandpass filters.

The frontend unit 120 includes the filterbank 121, its own internal (e.g. built-in) storage memory 122 and a sound level estimator 123. A sound level is estimated by the sound level estimator 123 per channel and/or summed across filter channels and is used to select the appropriate I/O function parameters.

Input/Output (I/O) gain functions (hereafter referred to as an "I/O functions") are stored on the memory 122 of the frontend unit 120. As is known in the art, I/O functions can be represented graphically showing how an output signal level (e.g. of a hearing aid) varies at various input signal levels. In this way, as is also known in the art, I/O functions can be used to determine the gain (in decibels), G (i.e. gain (G)=output (O)−input (I)) with respect to a given input (I) signal level. The I/O functions can also be used to determine a change in gain (ΔG) with respect to a change in given input (I) signal level. Sometimes, the change in gain (ΔG) is referred to as "compression".

The HLAI processing module 140 receives human-derived brain-processing information, to generate or derives human-derived Neural-Inspired Feedback Signals (NIFS) and stores them on its own internal (e.g. built-in) storage memory 142. To do this, the HLAI processing module 140 receives human-derived brain-processing information 144 (referring to parameters derived from brain recordings (direct ongoing, pre-recorded or generic human-derived datasets) and/or measurements derived by psychophysical/physiological assessments (direct ongoing, pre-recorded or generic human-derived datasets), and stores it on its internal memory 142 and, using said brain-processing information 144, the HLAI processing module 140 simulates: i) brainstem-mediated (BrM) neural feedback information and ii) cortical-mediated (CrM) neural feedback information (including information relating to attention). The HLAI processing module 140 then derives the human-derived NIFS using the simulated BrM and/or CrM neural feedback information and relays the NIFS to the frontend unit 120. In addition, the HLAI processing module 140 may store the derived NIFS on its internal memory 142. Alternatively, or additionally, the HLAI processing module 140 modifies the human derived NIFS in response to the received human-derived brain-processing information 144 and relays said NIFS to the frontend unit 120.

The HLAI processing module 140 is used to improve decision capability within the audio-signal processor 100. The brain-processing information 144 may include psychophysical, physiological, electroencephalographic (EEG) or other electrophysiological/electroencephalographic derived measurements, obtained by direct means (electroencephalographic (EEG) or other electrophysiological/electroencephalographic derived measurements) or indirect means (psychophysical, physiological), and be measured in real-time (ongoing) or pre-recorded and stored. The HLAI processing module 140 receives the brain-processing information 144 by a direct ongoing means of brain recordings from higher-levels of auditory processing areas of a human brain (e.g. from the brainstem/cortex), such as using EEG data (e.g., event-related, ongoing, oscillatory, attentional) retrieved from contact-electrodes, for example. Alternatively, the HLAI processing module 140 receives the brain-processing information 144 by a direct pre-recorded means of brain recordings (pre-recorded from either the user or generic human-derived datasets of higher-level processing from auditory processing areas and associated areas of a human brain). Alternatively, the HLAI processing module 140 receives the brain-processing information 144 by an indirect means (ongoing recorded from the user) derived by psychophysical/physiological assessments. Alternatively, the HLAI processing module 140 receives the brain-processing information 144 by an indirect means (pre-recorded from the user/generic human-derived datasets) derived by psychophysical/physiological assessments.

The pre-recorded and stored generic human-derived datasets may be updated as required. In both cases, (i.e. by using direct or indirect means) the brain-processing information 144 is derived from any one or a combination of the following: psychophysical data, physiological data, electrophysiological data, or electroencephalographic (EEG) data.

In use, the frontend unit 120 receives: an unfiltered input audio signal 111 from the receiving unit 110 and the human-derived NIFS from the HLAI processing module 140. The frontend unit 120 extracts sound level estimates from an output of the one or more bandpass filters of the filterbank 121, using the sound level estimator 123. In this way, the sound level estimator 123 estimates a sound level output from the array of overlapping filters.

The frontend unit 120 modifies the I/O function(s) stored on the memory 122 in response to the received sound level estimates and the NIFS and determines enhanced I/O function(s). As an I/O function is modified it becomes, as the names suggest, a more “enhanced” I/O function. The frontend unit 120 then stores the enhanced I/O function on its memory 122 (e.g. for reference or later use). The frontend unit 120 uses the enhanced I/O function to determine one or more modified filterbank parameters of the filterbank 121 in response to the received NIFS from the HLAI processing module 140. This is an “enhanced” I/O function as previous models have used only a “broken stick” function to model the I/O stage.

The one or more modified parameters determined by the enhanced I/O function include: i) a modified gain value and ii) a modified compression value for a given input audio signal. The frontend unit 120 stores the modified gain value and the modified compression value onto its memory 122. At a later time, the frontend unit 120 will retrieve the modified gain value and the modified compression value from its memory 122 and apply them to the unfiltered input audio signal 111 at the level of the filterbank 121, and determine a filtered output audio signal 112.

Referring to FIG. 1, in use, the audio-signal processor 100 performs a method of filtering an audio signal-of-interest. The method is performed by the processor 100 which includes the frontend unit 120, the frontend unit 120 includes a filterbank 121, a memory 122 with an input-output, I/O, function stored on said memory 122. The frontend unit 120 filters the input unfiltered input audio signal 111 and outputs a filtered audio signal 112. The output filtered audio signal 112 is relayed to the SFOD 130. The SFOD 130 is configured to receive the filtered output audio signal 112 from the frontend unit 120 and detect sound feature onsets 113. The SFOD 130 then relays the sound feature onsets 113 to the HLAI processing module 140, and the HLAI processing module 140 stores said sound feature onsets 113 onto its internal memory 142 for determining the NIFS. Advantageously, after front-end processing, the filtered output audio signal 112 is analysed to estimate sound feature onsets by the SFOD 130, as this is used to inform appropriate CrM and possibly BrM neural inspired feedback parameter selection for optimising speech enhancement.

As shown in FIG. 1, the SFOD 130 is further configured to relay the filtered output audio signal 112, as received from the frontend unit 120, to the HLAI processing module 140. The HLAI processing module 140 then stores the filtered output audio signal 112 on its internal memory 142. The HLAI processing module 140 receives human-derived brain-processing information 144 and stores it on its internal memory 142 and, using the brain-processing information 144, the HLAI processing module 140 simulates: the BrM and CrM neural feedback information. The HLAI processing module 140 then derives human-derived NIFS using the simulated BrM and/or CrM neural feedback information and stores the derived NIFS on its internal memory 142. After which, the HLAI processing module 140 relays the NIFS to the frontend unit 120.

As shown in FIG. 1, the receiving unit 110 first receives the unfiltered input audio signal 111, where the unfiltered input audio signal 111 comprises a mixture of the signal-of-interest (e.g. a speech signal) and background or ambient noise. The receiving unit 110 relays the unfiltered input audio signal 111 to the frontend unit 120. The frontend unit 120 then performs the following method steps: i) receiving:

an unfiltered input audio signal 111 (i.e. as received from the receiving unit 110), human-derived neural-inspired feedback signals, NIFS, (i.e. as received from the HLAI processing module 140), and ii) extracting sound level estimates from an output of the one or more bandpass filters of the filterbank 121 using the sound level estimator 123 (i.e. as received from the sound level estimator 123 in the frontend unit 120). iii) The frontend unit 120 then modifies the input-output, I/O, function(s) in response to the received sound level estimates, and the NIFS and iv) determines enhanced I/O function(s). After which, the frontend 120 then v) stores the enhanced I/O function(s) onto the memory 122, and vi) uses the enhanced I/O function(s) to determine one or more modified parameters in response to the received NIFS to modify the parameters associated with the filter(s) comprising the filterbank 121.

The method of adjusting the filter(s) of the filterbank 121 in response to the obtained one or more modified parameters includes: a modified gain value and a modified compression value for a given input audio signal. As such, the frontend unit 120 is further configured to perform the following method steps: vii) applying the modified gain value and the modified compression value to the unfiltered input audio signal 111, by adjusting parameters associated with the filter(s) of the filterbank 121, and then viii) determining a filtered output audio signal 112.

The human-derived brain-processing information 144 further includes a range of time constants ($\tau$). In simulating speech recognition effects using an ASR system the inventors have shown a beneficial effect of a range of time constants having any value between 50 to 2000 ms (Yasin et al 2020). The range of time constants ($\tau$) define a build-up and a decay of gain with time derived from human-derived measurements. The HLAI processing module 140 derives the human derived NIFS using said time constants and relays said NIFS to the frontend unit 120. Alternatively, or additionally, the HLAI processing module 140 modifies the human derived NIFS using said time constants in response to the received human-derived brain-processing information 144 and relays said NIFS to the frontend unit 120. The range of time constants are measured psychophysically from humans, typically covering the range 50-2000 ms. Optionally, the range of time constants may include values between 110 to 140 ms (Yasin et al., 2014). In other words, the HLAI processing module 140 uses information from the machine learning unit, higher-level brain processing data (i.e. BrM and CrM feedback data), sound feature onsets, SNR data, in order to optimise the parameters of the NIFS sent to be applied at the level of the frontend unit 120.

The BrM neural inspired feedback uses a range of human-derived onset and offset decay time constants ($\tau_{on}$ and $\tau_{off}$, respectively) associated with measured BrM neural feedback. The front-end gain and compression parameters are adaptable, dependent on the BrM neural-inspired feedback parameters, such as the time constants ($\tau_{on}$ and $\tau_{off}$). The range of time constants ($\tau$) includes onset time build-up constants ($\tau_{on}$). In response to receiving the human-derived brain-processing information 144 in the form of onset time build-up constants ($\tau_{on}$), the HLAI processing module 140 derives NIFS that are used by the frontend unit 120 to modify the enhanced I/O function(s) stored on the memory 122 of the frontend 120 to modify the rate of increase of the gain value applied to filter or filters of the filterbank 121. In this way, the onset time build-up constants, ($\tau_{on}$) can be considered "build-up of gain" time constants.

The range of time constants ($\tau$) may include offset time decay constants ($\tau_{off}$). In response to receiving the human-derived brain-processing information 144 in the form of offset time decay constants ($\tau_{off}$), the HLAI processing module 140 derives NIFS that are used by the frontend unit 120 to modify the enhanced I/O function(s) stored on the memory 122 of the frontend 120 to modify the rate of decrease of the gain value. In this way, the offset time decay constants ($\tau_{off}$) can be considered "decay in gain" time constants.

The BrM neural-inspired feedback is "tuned" across a given frequency range, and thus across one or more filters of the filterbank 121 (within the frontend 120 front-end) as shown to be the case in humans (Drga et al., 2016). This tuned BrM neural feedback response is adaptable, dependent on the auditory input and internal processing. In an example, the time constants ($\tau_{on}$ and $\tau_{off}$) associated with the BrM neural inspired feedback are dependent on the auditory input.

Frequency "tuning" of the neural feedback may be dependent on the strength of the feedback (and by association gain and compression modulation) as well as optimal parameters of the time-constants associated with the feedback. The neural feedback time course may comprise a range of time-constants (dependent on the audio input); values derived from either/both physiological data and human psychophysical data. The values of gain and compression (dependent on the audio input) and their modulation by the neural feedback will be modelled on human data. Published and unpublished datasets are used to model the front-end components of the processor. Yasin et al., (2014) have published methodologies that can be used in humans to estimate the time constants associated with this neurofeedback loop (these studies use unmodulated and unmodulated noise with a range of neural feedback time constants to estimate speech recognition in noise.

Modelled features of this data set (published (Yasin et al., 2014, Drga et al., 2016; Yasin et al., 2018; 2020) and unpublished) are used in the audio-signal processor to alter parameters of gain, compression and neural tuning, dependent on the time-constant of the neural feedback. Unpublished datasets (Yasin et al.) using modulated sounds (more representative of the external sounds and speech most often encountered) will also be used (providing a wider range of time constants associated with the neural feedback) to further enhance speech in noise. The modified gain values are a continuum of gain values, example values of which have already been described herein.

In response to the received NIFS, the frontend unit 120 may modify a bandwidth of one or more of each of the bandpass filters in the array of overlapping bandpass filters comprising the filterbank 121. In this way, the frontend unit 120 performs a process of "filter tuning "associated with the change in gain". The modified gain and compression values are either applied to the input audio signal 111 per bandpass filter in the array of overlapping bandpass filters. Alternatively, the modified gain and compression values are applied to the input audio signal 111 across some or all bandpass filters in the array of overlapping bandpass filters of the filterbank 121, within the frontend unit 120. The front-end gain and compression parameters are modelled using human-derived data in response to steady-state and modulated sounds.

Figure 2:
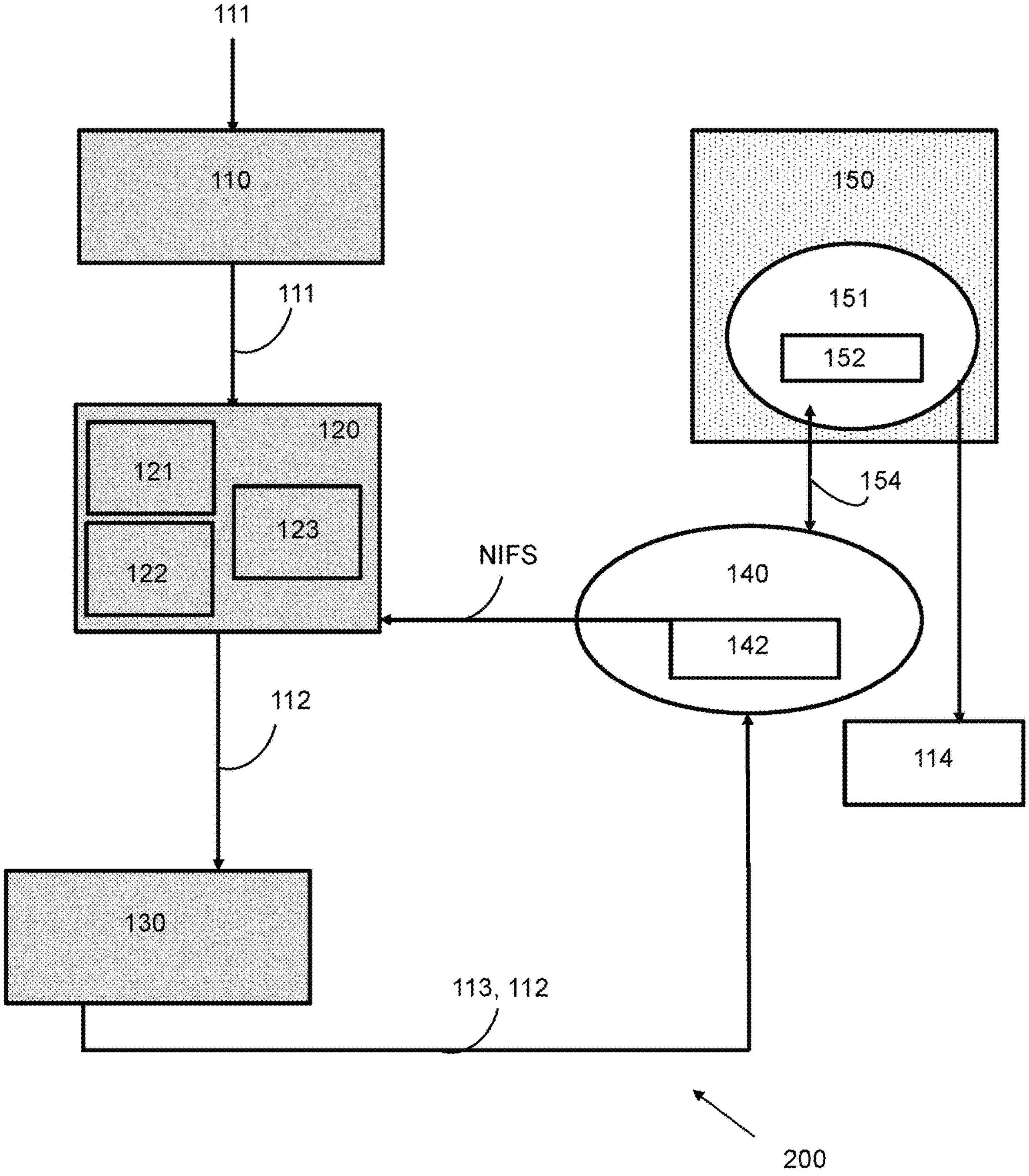
FIG. 2 shows an audio-signal processor according to another embodiment, which includes a machine learning unit (MLU)

FIG. 2 shows an audio-signal processor 200 according to another embodiment. The audio-signal processor 200 is the same as the audio-signal processor 100 shown in FIG. 1 with an inclusion of a machine learning unit (MLU) 150. The MLU 150 includes a decision device 151 in data communication 154 with the HLAI processing module 140. The decision device 151 comprising an internal (or built in) storage memory 152. As is the same in FIG. 1, the receiving unit 100, the frontend unit 120 and the SFOD 130 are all associated with front-end audio processing. The HLAI processing module 140 is associated with brain-inspired processing, incorporating HLAI and decision making, and the MLU 150 is associated with deep-learning based speech enhancement incorporating the HLAI and the decision making.

The decision device 151 receives data 154 from the HLAI processing module 140 and stores it on its internal memory 152. The data 154 may include the human-derived brain-processing information 144 as previously described. The data 154 may instead include anyone, or all, of the data that is stored on the internal memory 142 as previously described. For example, the data 154 may include any or all of the following: the human-derived brain-processing information 144 (with which to derive the simulated BrM feedback information and/or the simulated CrM neural feedback information), the derived or determined NIFS, the filtered output audio signal 112, and the sound feature onsets 113. As shown by the double-headed arrows in FIG. 2, the data 154 can be readily exchanged between the HLAI processing module 140 and the decision device 151 and/or the MLU 150. The decision device 150 of the MLU 150 then processes the data 154 and outputs a speech-enhanced filtered output audio signal 114. Alternatively, the MLU 150 outputs the speech-enhanced filtered output audio signal 114 after retrieving it from the memory 152 of the decision device 151.

Figure 3:
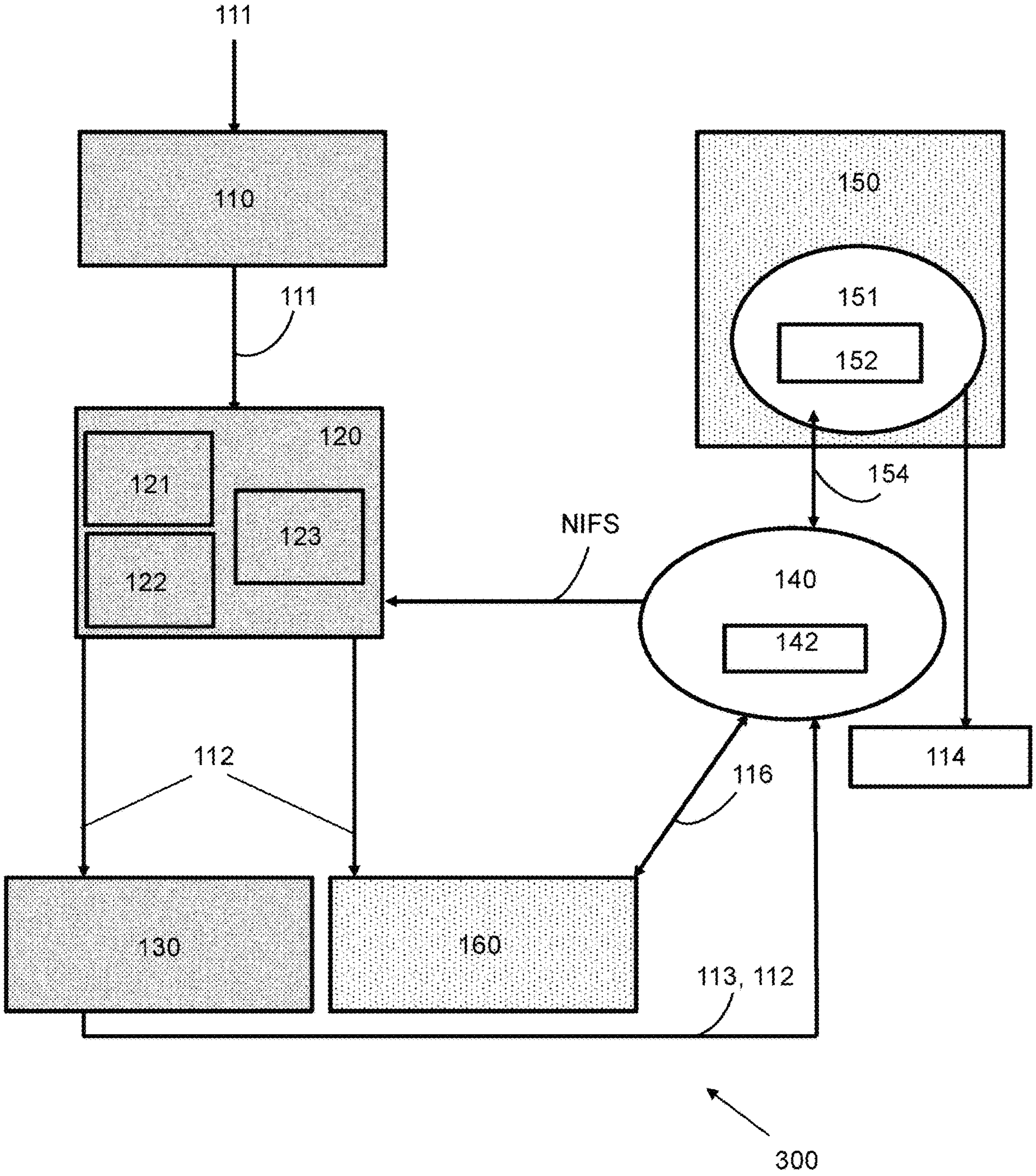
FIG. 3 shows an audio-signal processor according to another embodiment, which includes a Signal-to-Noise Ratio (SNR) estimator module.

FIG. 3 shows an audio-signal processor 300 according to another embodiment. The audio-signal processor 300 is the same as the audio-signal processor 200 shown in FIG. 2 with an inclusion of a Signal-to-Noise Ratio (SNR) estimator module 160. As is the same in FIG. 1 and FIG. 2, the receiving unit 100, the frontend unit 120 and the SFOD 130 are all associated with front-end audio processing. The SNR estimator module 160 and the HLAI processing module 140 are associated with brain-inspired processing, incorporating HLAI and decision making, and the MLU 150 is associated with deep-learning based speech enhancement incorporating the HLAI and the decision making.

The SNR estimator module 160 is in data communication with the frontend unit 120 and the HLAI processing module 140. The SNR estimator module 160 receives the filtered output audio signal 112 from the frontend unit 120 and determines a signal-to-noise ratio (SNR) values 116 of the filtered output audio signal 112. This determined SNR values 116 is a signal-to-noise ratio of the mixture of the signal-of-interest and the background noise plus parameters associated with the estimation. In one example, the SNR estimator module 160 uses a changing temporal window to determine an ongoing estimate of the signal-to-noise ratio (SNR) values 116 of the filtered output audio signal 112. The SNR estimator module 160 then relays the determined SNR values 116 to the HLAI processing module 140, and the HLAI processing module 140 stores the SNR values 116 on its memory 142 for determining the NIFS.

As shown by the double-headed arrows in FIG. 3, the SNR values 116 can be readily exchanged between the HLAI processing module 140 and the SNR estimator module 160. The data 154 may include anyone, or all, of the data that is stored on the internal memory 142 as previously described. For example, the data 154 may include any or all of the following: the human-derived brain-processing information 144 (in order to derive the simulated BrM feedback information and/or the simulated CrM neural feedback information), the derived or determined NIFS, the filtered output audio signal 112, the sound feature onsets 113, and the SNR values 116. As shown by the double-headed arrows in FIG. 3, the data 154 can be readily exchanged between the HLAI processing module 140 and the decision device 151 and/or the MLU 150. After front-end processing the filtered output audio signal 112 is analysed to estimate the SNR values 116 of the incoming speech-noise mixture, this is used to inform appropriate front-end parameter modification as well as feed into the decision device 151 for appropriate BrM and/or CrM neural inspired feedback parameter selection (aspects of which constitute the NIFS) for optimising speech enhancement.

Figure 4:
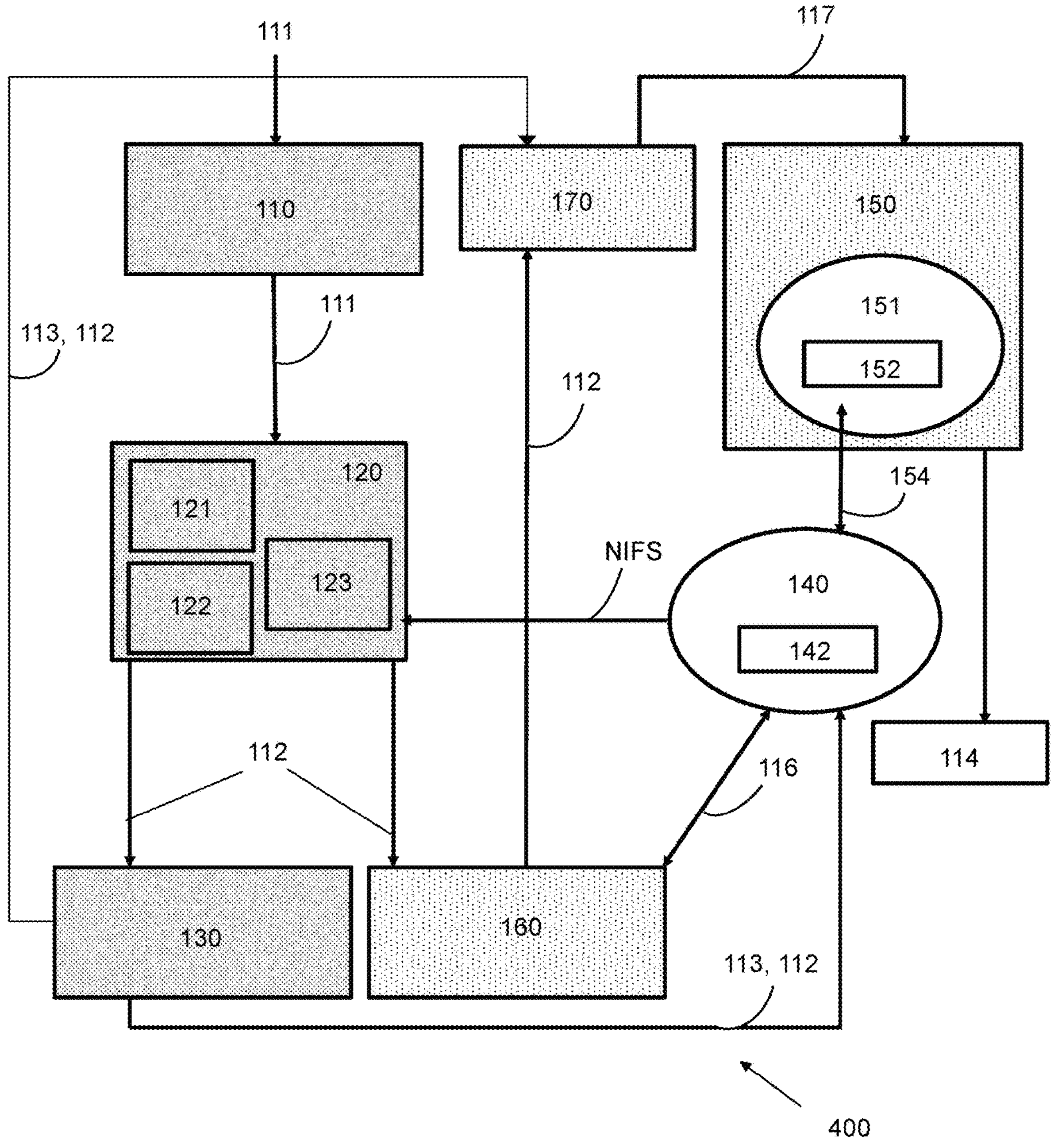
FIG. 4 shows an audio-signal processor according to another embodiment, which includes a feature extraction (FE) module.

FIG. 4 shows an audio-signal processor 400 according to another embodiment. The audio-signal processor 400 is the same as the audio-signal processor 300 shown in FIG. 3 with an inclusion of a feature extraction (FE) module 170. As is the same in FIGS. 1 to 3, the receiving unit 100, the frontend unit 120 and the SFOD 130 are all associated with front-end audio processing. The SNR estimator module 160, and the HLAI processing module 140 are associated with brain-inspired processing, incorporating HLAI and decision making, and the FE module 170 and MLU 150 is associated with deep-learning based speech enhancement incorporating the HLAI and the decision making.

The FE module 170 is in data communication with the SFOD 130, the SNR estimator module 160, and the MLU 150. The SNR estimator module 160 relays the filtered output audio signal 112 to the FE module 170. The FE module 170 then performs feature extractions on the filtered output audio signal 112 received from the SNR estimator module 160 in order to derive extracted features 117. The FE module 170 then relays extracted features 117 to the MLU 150, and the decision device 151 is configured to store the extracted features in its internal memory 152.

Alternatively, or additionally, as is shown in FIG. 4 the SFOD 130 relays the filtered output audio signal 112 to both the FE module 170 and the HLAI processing module 140 in addition to the detected sound feature onsets 113 as detected by the SFOD 130. The FE module 170 then performs feature extractions on the filtered output audio signal 112 received from the SFOD 130 in order to derive extracted features 117. The FE module 170 then relays extracted features 117 to the MLU 150, and the decision device 151 stores the extracted features in its internal memory 152. As is the same as the embodiment shown in FIG. 3, the data 154 may include anyone, or all, of the data that is stored on the internal memory 142 as previously described. For example, the data 154 may include any or all of the following: the human-derived brain-processing information 144 (data required to derive simulated BrM feedback information and/or the simulated CrM neural feedback information for the NIFS), the derived NIFS, the filtered output audio signal 112, the sound feature onsets 113, the SNR values 116, and the extracted features 117. As shown by the double-headed arrows in FIG. 4, the data 154 can be readily exchanged between the HLAI processing module 140 and the decision device 151 and/or the MLU 150.

In another embodiment, the HLAI processing module 140 modifies the human derived NIFS using said time constants in response to the received the data 154 (which at least includes: the filtered output audio signal 112, the sound feature onsets 113, and the SNR values 116) and relays said NIFS to the frontend unit 120.

The decision device 151 of the MLU 150 processes the data 154 received from, or exchanged between, the HLAI processing module 140. The data 154 includes the SNR values 116, which is readily exchanged between the HLAI processing module 140 and the SNR estimator module 160. In addition to the SNR values 116, the MLU 150 processes the extracted features 117 received directly from the FE module 170 and outputs a speech-enhanced filtered output audio signal 114. The decision device 151 also takes into account information regarding sound feature onsets and attentional oscillations that can be used to improve detection In summary of example working steps of the audio-processor 400 shown in FIG. 4, the filtered audio signal 112 of the frontend unit 120 is passed on to both the SFOD 130 and the SNR estimator module 160. Components of the filtered audio signal 112 are also passed on, from the SFOD 130 and SNR estimator module 160, to the FE module 170. Two-way communication of the SNR values 116 between the SNR estimator module 160 and the HLAI processing module 140, and two-way communication of data 154 between the HLAI processing module 140 and the MLU 150 allow for optimisation of the parameters comprising the NIFS sent to the frontend unit 120, and optimisation of the SNR estimator module 160 plus associated parameter values sent to the SNR estimator module 160. In this way, the audio-processor 400 produces at its output an enhanced filtered audio signal 114.

The MLU 150 includes a machine learning algorithm (not shown in the figures) that is stored on an internal memory, such as being stored on the internal memory 152 of the decision device 151. The decision device 151 applies an output of the algorithm to the data 154 received from the HLAI processing module 140 (which at least includes the SNR values 116) with the extracted features 117 received directly from the FE module 170 and derives neural-inspired feedback parameters. In this way, the SNR values 116 are combined with extracted features 117 and used to estimate appropriate neural-inspired feedback parameters using the MLU 150. The MLU 150 and/or the machine learning algorithm may be referred to as a "Semi-Supervised Deep Neural Network" or a "SSDNN". The SSDNN incorporates input from the HLAI to enhance speech detection in noisy backgrounds. For example, the decision device 151 uses inputs from the HLAI, the extracted features 117, the SNR values 116 and the SSDNN to optimise speech recognition in noise.

The machine learning algorithm encompasses a combination of both supervised and unsupervised learning using distributed embedded learning frames. The machine learning algorithm uses feature extraction information (i.e. the extracted features 117 directly received from the FE module 170) and the SNR values 116 contained in the data 154 (e.g. as received from the HLAI processing module 140) and "learns" dependencies between the signal and feature extraction. In other words, the audio-signal processor uses input from the HLAI processing module 140 to predict optimal Higher-Level Auditory Information (HLAI) over time. In other words, the SSDNN will "learn" over time (e.g. trained with a speech corpus with/without noise) and exposure to varied acoustic environments, the optimal parameters for speech enhancement in noise for a user. For example, the decision device 151 uses inputs from the HLAI, such as those contained within 154, extracted features 117, SNR values 116 and the SSDNN to optimise speech recognition in noise. The audio-signal processor parameters are optimised by the SSDNN over time. Measurements of brain derived HLAI will feed into a decision device 151 and aspects of the neural-inspired feedback process of the model.

The filtered output audio signal 112 may be analysed simultaneously by the SNR estimator module 160 to estimate the SNR values 116 and the FE module 170 to estimate the extracted features 117. Alternatively, the filtered output audio signal 112 may be analysed by the SNR estimator module 160 to estimate the SNR values 116 prior to the FE module 170, which is later used to estimate the extracted features 117.

The machine learning algorithm-derived neural-inspired feedback parameters are relayed, from the decision device 151 to the HLAI processing module 140 as part of the data 154 readily exchanged between the HLAI processing module 140 and the decision device 151 and/or the MLU 150. The HLAI processing module 140 then stores the neural-inspired feedback parameters on its memory 142 for determining the NIFS.

As an example, the decision device 151, within the SSDNN architecture of the signal processor 400, will incorporate oscillatory input information reflecting cortical and/or brainstem-level changes estimated from incoming stimulus-onset information that may be captured within 144 as well as elements of 130. The decision device 151 in conjunction with the SNR estimator module 160, via the HLAI 140, will inform optimal neural feedback parameter selection. Two-way interchange of information between 140 and decision device 151 will allow for further optimisation during a "training phase" of the SSDNN. In one example, the decision device 151 may combine information about CrM neural feedback (e.g. attentional processing, including attentional oscillations that can improve detection performance) obtained from human data and/or directly from brain from sensors placed in/or around the ear as captured by 144.

Figure 5:
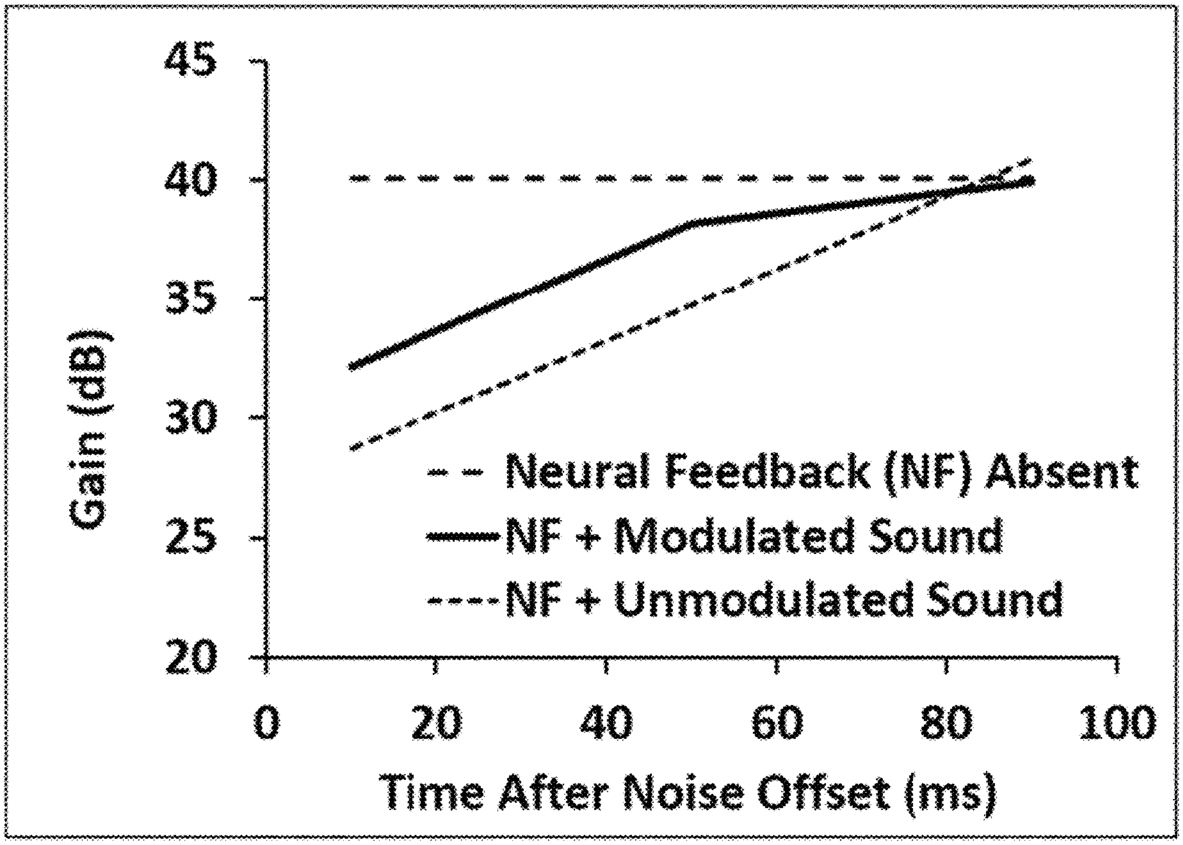
FIG. 5 shows a recovery of human auditory gain as a function of time elapsed from an end of Neural Feedback (NF) activation by a preceding noise, for modulated (solid line) and unmodulated (dotted line) sounds. Maximum auditory gain without activation of NF is shown by the dashed line.

FIG. 5 illustrates a recovery of human auditory gain as a function of time elapsed from an end of Neural Feedback (NF) activation by a preceding noise, for modulated (solid line) and unmodulated (dotted line) sounds. Maximum auditory gain without activation of NF is shown by the dashed line. FIG. 5 shows unpublished averaged datasets relevant to development of the front-end and feedback system of the audio-signal processor 100, 200, 300, 400, showing i) how activation of BrM neural feedback in humans can reduce the auditory gain (amplification) within 10-ms of the offset of background noise (enhancing the signal/speech), and ii) that the recovery of gain occurs at different rates for unmodulated and modulated sounds. Such parameters are used in the front-end of the audio-signal processor 100, 200, 300, 400.

The previously described SSDNN (or deep-neural network) and an incorporated decision device 151 are used to select the most appropriate temporal features, aspects of neural feedback, and noise/speech parameters to optimise speech enhancement. The combined inputs of feature extraction and SNR are used to feed into the machine-learning component of the model. SNR is estimated from the incoming speech and noise mixture, and used to select the appropriate feedback time constant for optimising speech enhancement in noise. To accomplish the SNR estimation the following published and unpublished datasets are used. Yasin et al., (2018) have published some of the relationships between the SNR and speech-recognition performance in steady-state noise using an alternative computational model. SNR-speech recognition performance functions, derived for both steady-state noise and a range of modulated noise are used to optimise performance of the (NIIAS) audio-signal processor 100, 200, 300, 400.

Yasin et al (2018; 2020), have published data showing how different neural time constants can be used to improve speech recognition in noise. The feasibility of using different neural-inspired time-constants for improved speech in noise (for differing background noise) has been demonstrated using a simple model, as shown in FIG. 6 and FIG. 7.

Figure 6:
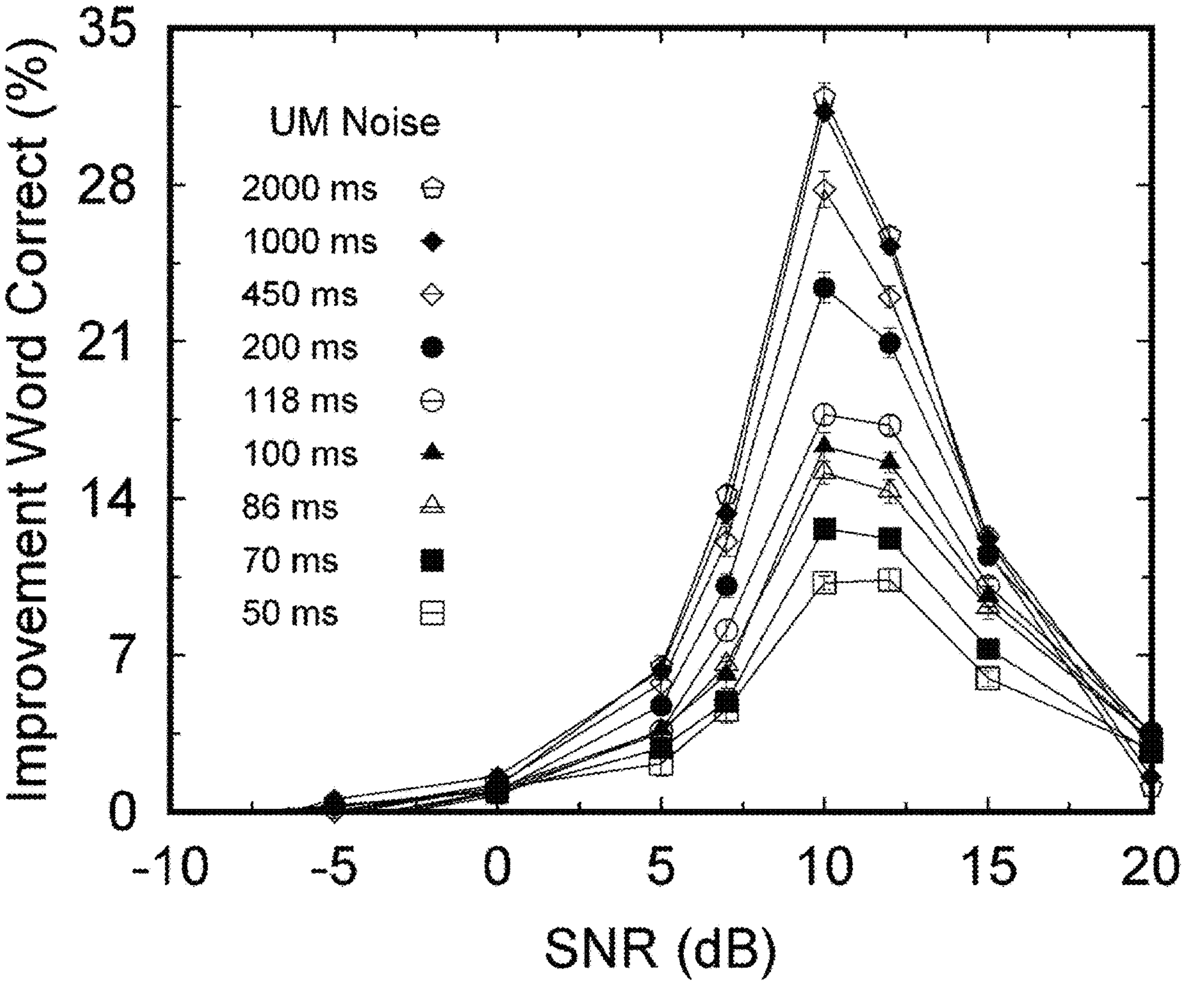
FIG. 6 illustrates an improvement in speech recognition (word correct) with a range of time constants in unmodulated noise.
Figure 7:
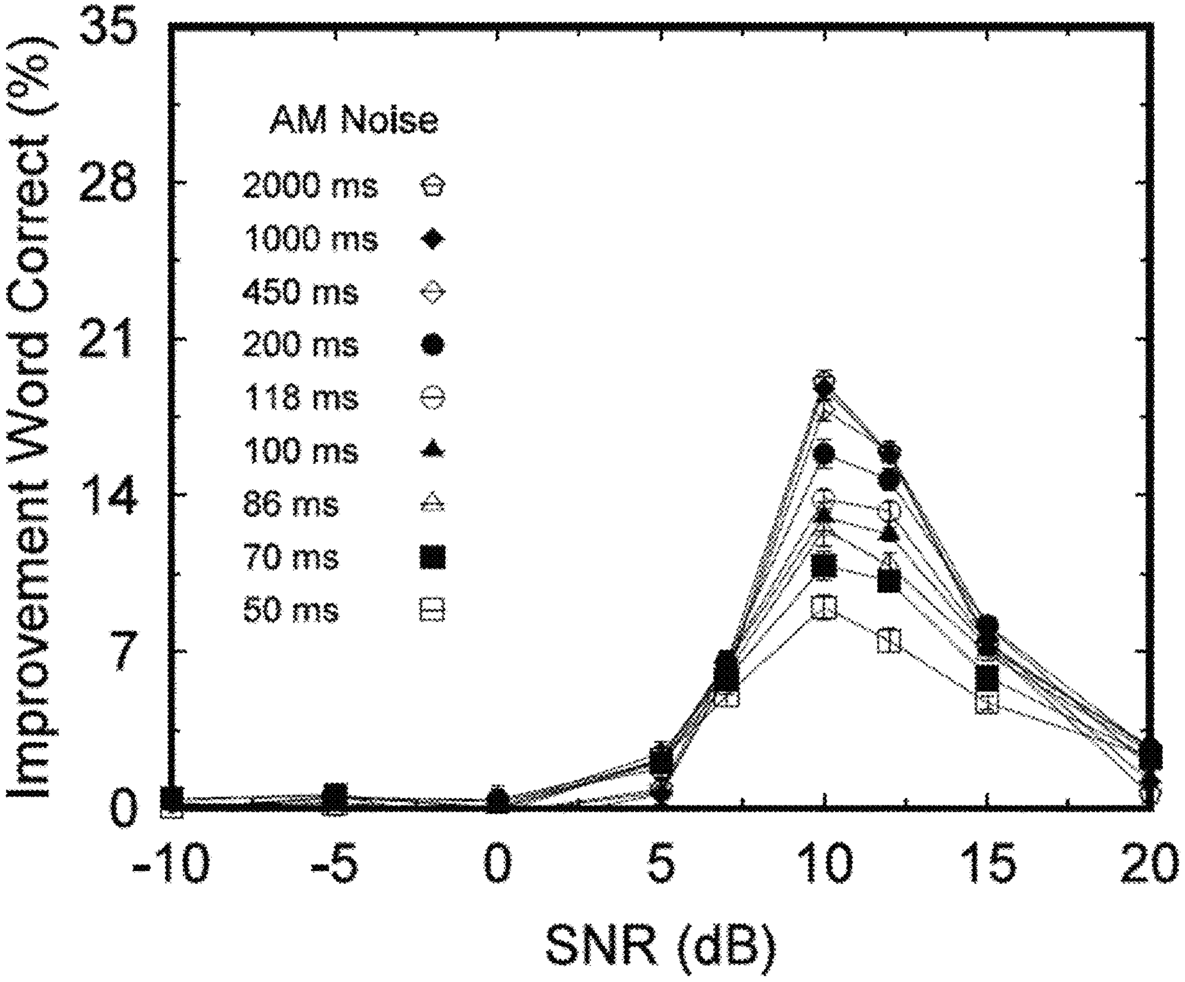
FIG. 7 illustrates an improvement speech recognition (word correct) with a range of time constants in modulated noise.

FIG. 6 illustrates an improvement in speech recognition (word correct) using an ASR with a range of neural-inspired time constants in unmodulated (steady-state) noise (Yasin et al., 2020), whereas FIG. 7 illustrates an improvement speech recognition (word correct) with a range of time constants in modulated noise (Yasin et al., 2020), using an alternative auditory computational model (Ferry and Meddis (2007)) comprising a filterbank, a neural inspired feedback and a speech recognition system (ASR). Some of this data, combined with unpublished data (such as that shown in FIG. 5), using additional time constants, signal and noise parameters are used in the neural feedback component of the (NIIAS) audio-signal processor 100, 200, 300, 400 to improve speech enhancement. FIG. 6 and FIG. 7 show output of feasibility studies using a limited set of components of an existing model front-end (without implementing the key novelties outlined above) to demonstrate feasibility of using different neural inspired time constants for differing audio inputs to improve speech recognition in noise. FIG. 5, FIG. 6 and FIG. 7 are relevant to the development of the front-end, elements of the neural feedback system and the SNR estimator.

Key Acronyms

AI: Artificial Intelligence
ASR: Automatic Speech Recognition
BrM: Brainstem-Mediated
CrM: Cortical-Mediated
EEG: Electroencephalography
FE: Feature Extraction
HLAI: Higher-Level Auditory Information
I/O: Input-Output
MOC: Medial OlivoCochlear
MLU: Machine Learning Unit
NIF: Neural-Inspired Feedback
NIIAS Processor: Neural-Inspired Intelligent Audio Signal Processor
SFOD: Sound Feature Onset Detector
SNR: Signal-to-Noise Ratio
SSDNN: Semi-Supervised Deep Neural Network
$\tau_{on}$ and $\tau_{off}$: Time-constants for the build-up and decay of gain, respectively

REFERENCES

Archbold, S., et al. (2014). The real cost of adult hearing loss, The Ear Foundation.
Ault, S. V., Perez, R. J., Kimble, C. A. and Wang, J., 2018. On speech recognition algorithms. *International Journal of Machine Learning and Computing,* 8(6), pp. 518-523.
Backus, B. C., and Guinan, J. J. Jr. (2006). Time course of the human medial olivocochlear reflex. J. Acoust. Soc. Am. 119, 2889-2904.
Brown, G. J., Ferry, R. T., and Meddis R. (2010). A computer model of auditory efferent suppression: Implications for the recognition in noise. J. Acoust. Soc. Am. 127, 943-954.
Cherry, E. C., 1953. Some experiments on the recognition of speech, with one and with two ears. *The Journal of the acoustical society of America,* 25(5), pp. 975-979.
Chintanpalli, A., Jennings, S. G., Heinz, M. G., and Strickland, E. (2012). Modelling the anti-masking effects of the olivocochlear reflex in auditory nerve responses to tones in sustained noise. Journal of Research in Otolayngology, 13, 219-235.
Chung, K. (2004). "Challenges and recent developments in hearing aids: Part I: Speech understanding in noise, microphone technologies and noise reduction algorithms. Trends in Amplification, 8(3), 83-124.
Clark, N. R., Brown, G. J., Jürgens, T., and Meddis, R. (2012). A frequency-selective feedback model of auditory efferent suppression and its implications for the recognition of speech in noise. J. Acoust. Soc. Am. 132, 1535-1541.
Cooper, N. P., and Guinan, J. J. (2003). Separate mechanical processes underlie fast and slow effects of medial olivocochlear efferent activity. J. Physiol. 548, 307-312.
Dillon, H., Zakis, J. A., McDermott, H., Keidser, G., Dreschler, W., and Convey, E., (2006). "The trainable hearing aid: What will it do for clients and clinicians?" The Hearing Journal, 59(4), 30.
Drga, V., Plack, C. J. and Yasin, I., (2016). "Frequency tuning of the efferent effect on cochlear gain in humans," In: Physiology, Psychoacoustics and Cognition in Normal and Impaired Hearing (Eds. P. van Dijk, Baskent, D., Gaudrain, E., de Kleine, E., Wagner, A., Lanting, C.), Springer-Verlag, Heidelberg, pp 477-484. ISBN: 978-3-319-25472-2.
Ferry, R. T., and Meddis, R. (2007). A computer model of medial efferent suppression in the mammalian auditory system. J. Acoust. Soc. Am. 122, 3519-3526.
Gao, Y., Wang, Q., Ding, Y., Wang, C., Li, H., Wu, X., Qu, T. and Li, L., 2017. Selective attention enhances beta-band cortical oscillation to speech under "Cocktail-Party" listening conditions. *Frontiers in human neuroscience,* 11, p. 34.
Ghitza, O. (1988) Auditory neural feedback as a basis for speech processing. In ICASSP-88., International Conference on Acoustics, Speech, and Signal Processing (91-94). IEEE.
Giraud, A. L., Garnier, S., Micheyl, C., Lina, G., Chays, A., and Chery-Croze S. (1997). Auditory efferents involved in speech-in-noise intelligibility. NeuroRep. 8, 1779-1783.
Guinan Jr, J. J. and Stankovic, K. M., 1996. Medial efferent inhibition produces the largest equivalent attenuations at moderate to high sound levels in cat auditory-nerve fibers. *The Journal of the Acoustical Society of America,* 100(3), pp. 1680-1690.
Guinan Jr, J. J., 2018. Olivocochlear efferents: Their action, effects, measurement and uses, and the impact of the new conception of cochlear mechanical responses. *Hearing research,* 362, pp. 38-47.
Guinan Jr, J. J. (2010). Cochlear efferent innervation and function. Current Opinion in Otolaryngology and Head and Neck Surgery, 18(5), 447-453.
Hear-it AISBL (October 2006), www.hear-it.org.
Hedrick, M. S., Moon, I. J., Woo, J. and Won, J. H., 2016. Effects of physiological internal noise on model predictions of concurrent vowel identification for normal-hearing listeners. *PloS one,* 11(2), p. e0149128.
Heinz, M. G., Zhang, X., Bruce, I. C., and Carney, L. H. (2001). "Auditory nerve model for predicting performance limits of normal and impaired listeners". Acoustics Research Letters Online, 2(3), 91-96.
Ho, H. T., Leung, J., Burr, D. C., Alais, D. and Morrone, M. C., 2017. Auditory sensitivity and decision criteria oscillate at different frequencies separately for the two ears. *Current Biology,* 27(23), pp. 3643-3649.

Horton, R. (2016). "Hearing Loss: an important global health concern", Lancet, 387(10036), 2351.

The Institute of Acoustics. InstituteofAcoustics(UK).https://www.ioa.or.uk/

Jürgens, T., Clark, N. R., Lecluyse, W. and Ray, M., 2014. The function of the basilar membrane and medial olivocochlear (MOC) reflex mimicked in a hearing aid algorithm. *The Journal of the Acoustical Society of America,* 135(4), pp. 2385-2385.

Jennings, S. G. and Strickland, E. A., 2010. The frequency selectivity of gain reduction masking: analysis using two equally-effective maskers. In *The Neurophysiological Bases of Auditory Perception* (pp. 47-58). Springer, New York, NY.

Jennings S G, Strickland E A (2012) Evaluating the effects of olivocochlear feedback on psychophysical measures of frequency selectivity. The Journal of the Acoustical Society of America 132 (4): 2483-2496.

Jürgens, T., Clark, N. R., Lecluyse, W. and Meddis, R., 2016. Exploration of a physiologically-inspired hearing-aid algorithm using a computer model mimicking impaired hearing. *International journal of audiology,* 55(6), pp. 346-357.

Kawase, T., Delgutte, B., and Liberman, M. C. (1993). Antimasking effects of the olivocochlear reflex. II. Enhancement of auditory-nerve response to masked tones. J. Neurophysiol. 70, 2533-2549.

Kuo, S. M., Kuo, K. and Gan, W. S., 2010, June. Active noise control: Open problems and challenges. In *The* 2010 *International Conference on Green Circuits and Systems* (pp. 164-169). IEEE.

Lauzon, A., 2017. Attentional Modulation of Early Auditory Responses. *neurology,* 51(1), pp. 41-53.

Liberman, M. C., Puria, S., & Guinan, J. J. Jr. (1996). "The ipsilaterally evoked olivocochlear reflex causes rapid adaptation of the 2 f 1-f 2 distortion product otoacoustic emission," J. Acoust. Soc. Am. 99, 3572-3584.

Lopez-Poveda, E. A., Eustaquio-Martin, Stohl, J. S., Wolford, R. D., Schatzer, R., and Wilson, B. S. (2016). A Binaural cochlear implant sound coding strategy inspired by the contralateral medial olivocochlear reflex. Ear and Hearing, 37, e138-e148.

Lopez-Poveda E. A. (2017). US Patent Sound Enhancement for Cochlear Implants. US 2017/0043162 A1

Maison, S., Micheyl, C. and Collet, L., 1997. Medial olivocochlear efferent system in humans studied with amplitude-modulated tones. *Journal of neurophysiology,* 77(4), pp. 1759-1768.

Maison, S., Micheyl, C., and Collet, L. (1999). Sinusoidal amplitude modulation alters contralateral noise suppression of evoked optoacoustic emissions in humans. Neurosci. 91, 133-138.

Martin, R. (2001). "Noise power spectral density estimation based on optimal smoothing and minimum statistics". IEEE Transactions on speech and audio processing, 9(5), 504-512.

May, T., Kowalewski, B., Fereczkowski, M., and MacDonald, E. N. (2017). "Assessment of broadband SNR estimation for hearing aid applications". In Acoustics, Speech and Signal Processing (ICASSP), IEEE International Conference on. 231-235. IEEE.

Meddis, R., O'Mard, L. P., and Lopez-Poveda, E. A. (2001). "A computational algorithm for computing nonlinear auditory frequency selectivity". The Journal of the Acoustical Society of America, 109(6), 2852-2861.

Messing, D. P., Delhorne, L., Bruckert, E., Braida, L., and Ghitza, O. (2009). A non-linear efferent-inspired model of the auditory system; matching human confusions in stationary noise. Speech Comm. 51, 668-683.

Russell, I. J. and Murugasu, E., 1997. Medial efferent inhibition suppresses basilar membrane responses to near characteristic frequency tones of moderate to high intensities. *The Journal of the Acoustical Society of America,* 102(3), pp. 1734-1738.

The NewsStack, 2019: https://thenewstack.io/speech-recognitiongettingsmarterstate.art.speech-recognition/

NIH, 2018: "Accessible and affordable hearing health care activities" (2017). https://www.nidcd.nih,gov/research/improvehearing-health-care. Accessed on 31 Dec. 2018

Office for National Statistics(2014).https://www.ons.gov.uk/peoplepopulationandcomunity. Accessed 31 Dec. 2018.

Russell, I. J., and Murugasu, E. (1997). Medial efferent inhibition suppresses basilar membrane responses to near characteristic frequency tones of moderate to high intensities. J. Acoust. Soc. Am. 102, 1734-1738.

Strickland, E. A., 2008. The relationship between precursor level and the temporal effect. *The Journal of the Acoustical Society of America,* 123(2), pp. 946-954.

Strickland, E. A. and Krishnan, L. A., 2005. The temporal effect in listeners with mild to moderate cochlear hearing impairment. *The Journal of the Acoustical Society of America,* 118(5), pp. 3211-3217.

Smalt, C. J., Heinz, M. G., and Strickland, E. A. (2014). Modelling the time-varying and level-dependent effects of the medial olivocochlear reflex in auditory nerve responses, J. Assoc. Res. Otolaryngol, 15, 159-173.

Taylor, R. S. and Paisley, S., 2000. The clinical and cost effectiveness of advances in hearing aid technology [report to the National Institute of Clinical Excellence (NICE)].

Taylor, R. S., Paisley, S. and Davis, A., 2001. Systematic review of the clinical and cost effectiveness of digital hearing aids. *British journal of audiology,* 35(5), pp. 271-288.

The Top500. https://www.top500.org/news/uk-commits-a-billion-pounds-to-ai-development/

UN Agenda (2030), 2018: "The 2030 Agenda for Sustainable Development and the SDGs". http://ec.europa.eu/environment/sustainabledevelopment/SDGs/index-_en.htm. Accessed on 31 Dec. 2018.

UNICEF (2018). UNICEF Supply; Disabilities. https://www.unicef.org/disabilities/index_82460.html. Accessed on 31 Dec. 2018.

Vondrasek, M. and Pollak, P., 2005. Methods for speech SNR estimation: Evaluation tool and analysis of VAD dependency. *Radioengineering,* 14(1), pp. 6-11.

Verhey, J. L., Kordus, M., Drga, V. and Yasin, I., 2017. Effect of efferent activation on binaural frequency selectivity. *Hearing Research,* 350, pp. 152-159.

Verhey, J. L., Ernst, S. E., and Yasin, I. (2012). "Effects of sequential streaming on auditory masking using psychoacoustics and auditory evoked potentials," Hear. Res. 285, 77-85. DOI: 10.1016/j.heares.2012.01.006.

Warren III, E. H. and Liberman, M. C., 1989. Effects of contralateral sound on auditory-nerve responses. I. Contributions of cochlear efferents. *Hearing research,* 37(2), pp. 89-104.

Wayne, R. V. and Johnsrude, I. S., 2015. A review of causal mechanisms underlying the link between age-related hearing loss and cognitive decline. *Ageing research reviews,* 23, pp. 154-166.

Winslow, R. L. and Sachs, M. B., 1988. Single-tone intensity discrimination based on auditory-nerve rate responses in backgrounds of quiet, noise, and with stimulation of the crossed olivocochlear bundle. *Hearing research,* 35(2-3), pp. 165-189.

World Health Organization (2012). "WHO global estimates on prevalence of hearing loss".

WHO Priority Assistive Products List, 2016: "Priority Assistive Products List (APL). (2016). https://www.who.int/phi/implementation/assistive_technology/global_survey-apl/en/. Accessed on 31 Dec. 2018.

Yasin, I., Drga, V., & Plack, C. J. (2014). "Effect of human auditory efferent feedback on cochlear gain and compression," J. Neurosci. 12, 15319-15326.

Yasin, I., Drga, V., Liu, F., Demosthenous, A., et al. (2020). Optimizing speech recognition using a computational model of human hearing: Effect of noise type and efferent time constants. IEEE Access, 8, 56711-56719.

Yasin, I., Liu, F., Drga, V., Demosthenous, A. et al. (2018). Effect of auditory efferent time-constant duration on speech recognition in noise. J. Acoust. Soc. Am., 143, EL112-EL115.

Yu, H., Tan, Z. H., Ma, Z., Martin, R. and Guo, J., 2017. Spoofing detection in automatic speaker verification systems using DNN classifiers and dynamic acoustic features. *IEEE transactions on neural networks and learning systems*, (99), pp. 1-12.

Zeng, F. G., and Liu, S. (2006). Speech perception in individuals with auditory neuropathy. J. Speech, Lang. Hear. Res. 49: 367-380.

The invention claimed is:

1. An audio-signal processor for filtering an audio signal-of-interest from an input audio signal comprising a mixture of the audio signal-of-interest and background noise, the processor comprising a frontend unit, the frontend unit comprising a filterbank comprised of an array of bandpass filters, a sound level estimator, and a memory with one or more input-output, I/O, functions stored on said memory; wherein the frontend unit is configured to receive:

an unfiltered input audio signal, and human-derived neural-inspired feedback signals, NIFS, wherein the frontend unit is further configured to:

extract sound level estimates from an output of the one or more bandpass filters using the sound level estimator, modify the input-output, I/O, functions in response to the received sound level estimates and the NIFS, and determine enhanced I/O functions, and store the enhanced I/O functions on the memory and use the enhanced I/O functions to determine one or more modified filterbank parameters in response to the received NIFS and sound level estimates, wherein the one or more modified filterbank parameters include: i) a modified gain value and ii) a modified compression value for a given input audio signal, apply the modified filterbank parameters either across one filter of the filterbank or across a range of filters of the filterbank within the frontend unit, wherein the frontend unit is further configured to: apply the modified gain value and the modified compression value to the unfiltered input audio signal by way of modifying the input or parameters of a given filter or range of filters of the filterbank to determine a filtered output audio signal, and output the filtered audio signal to a sound feature onset detector for further processing.

2. The audio-signal processor of claim 1, wherein the processor further comprises:

a Higher-Level Auditory Information, HLAI, processing module, comprising an internal memory, the HLAI processing module configured to receive human-derived brain-processing information and/or measurements derived by psychophysical/physiological assessments, and store it on its internal memory and, using said brain-processing information, the HLAI is further configured to simulate aspects of the following, which constitute aspects of the NIFS:

brainstem-mediated, BrM, neural feedback information and cortical-mediated, CrM, neural feedback information.

3. The audio-signal processor of claim 2, wherein the HLAI processing module is further configured to derive the human-derived NIFS using said simulated and/or direct BrM and/or CrM neural feedback information and relay said NIFS to the frontend unit.

4. The audio-signal processor of claim 2, wherein the HLAI processing module is configured to receive the brain-processing information by direct means or by indirect means from higher-levels of auditory processing areas of a human brain, and wherein the brain-processing information is derived from any one of, or a combination of, the following: psychophysical data, physiological data, electrophysiological data, or electroencephalographic (EEG) data.

5. The audio-signal processor of claim 2, wherein the human-derived brain-processing information further comprises a range of time constants which define a build-up and a decay of gain with time derived from human-derived measurements; and wherein HLAI processing module is further configured to modify the human-derived NIFS using said time constants in response to the received brain-processing information and relay said NIFS to the frontend unit.

6. The audio-signal processor of claim 5, wherein the range of time constants comprise human-derived onset time build-up constants, $\tau_{on}$, applied to the I/O functions stored in the frontend unit to modify the I/O functions and derive the enhanced I/O functions stored in the frontend unit to modify a rate of increase of the gain value, effects of which are subsequently applied to the filter or filters of the filterbank.

7. The audio-signal processor of claim 5, wherein the range of time constants comprise human-derived offset time decay constants, $\tau_{off}$, applied to the I/O functions stored in the frontend unit to modify the I/O functions and derive the enhanced I/O functions stored in the frontend unit to modify a rate of decrease of the gain value, effects of which are subsequently applied to the filter or filters of the filterbank.

8. The audio-signal processor of claim 2, further comprising a sound feature onset detector configured to receive the filtered output audio signal from the frontend unit and detect sound feature onsets, and wherein the sound feature onset detector is further configured to relay the sound feature onsets to the HLAI processing module, and the HLAI processing module is configured to store said sound feature onsets on its internal memory for determining the NIFS.

9. The audio-signal processor of claim 8, wherein the sound feature onset detector is further configured to relay the filtered output audio signal to the HLAI processing module and the HLAI processing module configured to store the filtered output audio signal on its internal memory.

10. The audio-signal processor of claim 2, further comprising a signal-to-noise ratio, SNR, estimator module configured to receive the filtered output audio signal from the frontend unit and determine a SNR of the mixture of the signal-of-interest and the background noise, and wherein the SNR estimator module is further configured to relay the SNR to the HLAI processing module, and the HLAI processing module is configured to store said SNR on its memory for determining the NIFS.

11. The audio-signal processor of claim 10, further comprising a machine learning unit comprising a decision device in data communication with the HLAI processing module, the decision device comprising an internal memory, the decision device is configured to receive data from the HLAI processing module and store it on its internal memory, wherein the decision device is configured to process the data and output a speech-enhanced filtered output audio signal.

12. The audio-signal processor of claim 11, further comprising a feature extraction, FE, module, said FE module is further configured to perform feature extraction on the filtered output audio signal, and the FE module is further configured to relay the extracted features to the machine learning unit, and the decision device is configured to store the extracted features in its internal memory.

13. The audio-signal processor of claim 12, wherein the SNR estimator module is configured to relay the filtered output audio signal to the FE module, the FE module is configured to relay the filtered output audio signal to the machine learning unit, and the decision device is configured to store the filtered output audio signal in its internal memory.

14. The audio-signal processor of claim 11, wherein the decision device is configured to process:

the data received from the HLAI processing module, which includes the SNR values, the extracted features, sound feature onsets and attentional oscillations data, and outputs a speech-enhanced filtered output audio signal.

15. The audio-signal processor of claim 14, wherein the machine learning unit further comprises a machine learning algorithm stored on its internal memory, and wherein the decision device applies an output of the algorithm to the data received from the HLAI processing module, including the SNR values, the extracted features, and derives neural-inspired feedback parameters.

16. The audio-signal processor of claim 15, wherein the derived neural-inspired feedback parameters are relayed, from the decision device, to the HLAI processing module and the HLAI processing module is configured to store said neural-inspired feedback parameters on its memory for determining the NIFS.

17. The audio-signal processor of claim 1, wherein the modified gain values are a continuum of gain values, derived from human data that are in the following range: 10 to 60 dB.

18. The audio-signal processor of claim 1, wherein the modified compression values are a continuum of compression values that are in the following range: 0.1 to 1.0.

19. The audio-signal processor of claim 18, wherein the continuum of compression values are derived from human datasets and are dependent on input sound aspects, wherein the input sound aspects comprise a sound level and temporal characteristics which define the compression applied.

20. The audio-signal processor of claim 1, wherein the filter or filters of the filterbank within the frontend unit is further configured so as to modify a bandwidth of each of the one or more bandpass filters.

21. The audio-signal processor of claim 1, wherein the modified gain and compression values are:

either applied to the input audio signal per bandpass filter in the one or more bandpass filters, or are applied to the input audio signal across some or all bandpass filters in the one or more bandpass filters.

22. A method of filtering an audio signal-of-interest from an input audio signal comprising a mixture of the audio signal-of-interest and background noise, the method performed by a processor comprising a frontend unit, the frontend unit comprising a filterbank, the filterbank comprising one or more bandpass filters, a sound level estimator, and a memory with an input-output, I/O, functions stored on said memory, wherein the frontend unit is configured to perform the following method steps:

i) receiving:

an unfiltered input audio signal, human-derived neural-inspired feedback signals, NIFS, ii) extracting sound level estimates from an output of the one or more bandpass filters using the sound level estimator, iii) modifying the input-output, I/O, functions in response to the received sound level estimates and the NIFS, iv) determining an enhanced I/O function, v) storing the enhanced I/O function on said memory, vi) using the enhanced I/O function to determine one or more modified parameters to apply to the filter/filters of the filterbank in response to the received NIFS, wherein the one or more modified filterbank parameters include: i) a modified gain value and ii) a modified compression value for a given input audio signal, vii) applying the modified filterbank parameters either across one filter of the filterbank or across a range of filters of the filterbank within the frontend unit, wherein the frontend unit is further configured to: apply the modified gain value and the modified compression value to the unfiltered input audio signal by way of modifying the input or parameters of a given filter or range of filters of the filterbank to determine a filtered output audio signal, and viii) outputting the filtered audio signal to a sound feature onset detector for further processing.

* * * * *